United States Patent
Usuda

(10) Patent No.: US 11,288,550 B2
(45) Date of Patent: Mar. 29, 2022

(54) DATA PROCESSING APPARATUS AND METHOD, RECOGNITION APPARATUS, LEARNING DATA STORAGE APPARATUS, MACHINE LEARNING APPARATUS, AND PROGRAM

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 17 days.

(21) Appl. No.: 16/927,987

(22) Filed: Jul. 13, 2020

(65) Prior Publication Data

US 2020/0342267 A1 Oct. 29, 2020

Related U.S. Application Data

(63) Continuation of application No. PCT/JP2018/046747, filed on Dec. 19, 2018.

(30) Foreign Application Priority Data

Jan. 30, 2018 (JP) .............................. JP2018-013764

(51) Int. Cl.
*G06K 9/00* (2022.01)
*G06K 9/62* (2022.01)
*G06T 7/00* (2017.01)

(52) U.S. Cl.
CPC ......... *G06K 9/6262* (2013.01); *G06K 9/6254* (2013.01); *G06T 7/0012* (2013.01);
(Continued)

(58) Field of Classification Search
CPC .. G06K 9/6262; G06K 9/6254; G06K 9/6271; G06K 2209/05; G06T 7/0012;
(Continued)

(56) References Cited

U.S. PATENT DOCUMENTS

2003/0169352 A1* 9/2003 Kitani ................ H04N 5/23245
348/247
2016/0344952 A1* 11/2016 Ichihara .................. G06T 5/003

FOREIGN PATENT DOCUMENTS

JP H03102477 4/1991
JP H04090076 3/1992
(Continued)

OTHER PUBLICATIONS

H. Nosato, H. Sakanashi, E. Takahashi and M. Murakawa, "An objective evaluation method of ulcerative colitis with optical colonoscopy images based on higher order local auto-correlation features," 2014 IEEE 11th International Symposium on Biomedical Imaging (ISBI), 2014, pp. 89-92. (Year: 2014).*
(Continued)

*Primary Examiner* — Van D Huynh
(74) *Attorney, Agent, or Firm* — JCIPRNET

(57) ABSTRACT

A data processing apparatus and a method, a recognition apparatus, a learning data storage apparatus, a machine learning apparatus, and a program capable of improving recognition accuracy for data of a rare case are provided. A data processing apparatus according to one aspect of the present invention includes a recognition unit that learns using a learning data set, a recognition result correction unit that corrects a recognition result of the recognition unit for data acquired through a data acquisition unit in accordance with an instruction from a user, and a machine learning unit that performs learning of the recognition unit using the data in which the recognition result is corrected. The machine learning unit performs learning of the recognition unit by setting a degree of contribution to learning from the data in which the recognition result is corrected to be higher than a degree of contribution to learning of the recognition unit from learning data included in the learning data set.

22 Claims, 16 Drawing Sheets

(52) U.S. Cl.
CPC ............... *G06T 2207/20081* (2013.01); *G06T 2207/20084* (2013.01); *G06T 2207/30096* (2013.01)

(58) Field of Classification Search
CPC . G06T 2207/20081; G06T 2207/20084; G06T 2207/30096; G16H 30/40; G16H 50/20; G06N 20/00
USPC .......................................................... 382/128
See application file for complete search history.

(56) References Cited

FOREIGN PATENT DOCUMENTS

| | | | |
|---|---|---|---|
| JP | 2002345862 | | 12/2002 |
| JP | 200549968 | * | 2/2005 |
| JP | 2005049968 | | 2/2005 |
| JP | 2005339322 | | 12/2005 |
| JP | 2015230570 | * | 12/2015 |
| JP | 2016006617 | | 1/2016 |
| JP | 5953384 | | 7/2016 |
| JP | 2016143352 | * | 7/2016 |
| JP | 2017162098 | | 9/2017 |
| WO | 2017158058 | | 9/2017 |

OTHER PUBLICATIONS

"Office Action of Japan Counterpart Application", dated Apr. 26, 2021, with English translation thereof, p. 1-p. 8.

Narukawa, Hiroki et al., "Improvement of the Extraction of the Iteration between Supervised Drugs Using Knowledgebase," Proceedings of the 20th Annual Meeting of the Association for Natural Language Processing, Mar. 10, 2014, with concise explanation of relevance of Document 7 from English translation of Form PCT/ISA/237, pp. 1-8.

Hirokazu Nosato, et al., "Objective Evaluation Method for Optical Colonoscopy based on Image Recongition." IPSJ SIG Technical Reports, vol. 2012-MPS-91, Feb. 15, 2013, pp. 1-6.

Yukitaka Nimura, et al., "A Study on quantifying emphysema severity by using multi-class classifier based on combining CT image and spirometric measurements." IEICE Technical Report, vol. 110, No. 121, Jul. 2, 2010, pp. 57-62.

Hiroki Narukawa, et al., "Improvement of the Extraction of the Iteration between Supervised Drugs Using Knowledgebase." Proceedings of the 20th Annual Meeting of the Association for Natural Language Processing, Mar. 10, 2014, with concise explanation of relevance from English translation of Form PCT/ISA/237, pp. 995-998.

"International Search Report (Form PCT/ISA/210)" of PCT/JP2018/046747, dated Feb. 19, 2019, with English translation thereof, pp. 1-5.

"Written Opinion of the International Searching Authority (Form PCT/ISA/237)" of PCT/JP2018/046747, dated Feb. 19, 2019, with English translation thereof, pp. 1-10.

"Office Action of Japan Counterpart Application", dated Aug. 6, 2021, with English translation thereof, p. 1-p. 6.

* cited by examiner

FIG. 2

| IMAGE | CORRECT ANSWER | CORRECTION | WEIGHT |
|---|---|---|---|
| 000.jpg | POSITIVE | NOT MADE | 1.0 |
| 001.jpg | POSITIVE | MADE | 2.0 |
| 002.jpg | NEGATIVE | NOT MADE | 1.0 |
| ⋮ | ⋮ | ⋮ | ⋮ |

FIG. 6

| IMAGE | CORRECT ANSWER | CORRECTION | WEIGHT |
|---|---|---|---|
| 000.jpg | POSITIVE | NOT MADE | 1.0 |
| 001.jpg | POSITIVE | MADE | 5.0 |
| 002.jpg | POSITIVE | MADE | 2.0 |
| ⋮ | ⋮ | ⋮ | ⋮ |

FIG. 8

| IMAGE | CORRECT ANSWER | CORRECTION | SEVERITY | WEIGHT |
|---|---|---|---|---|
| 000.jpg | POSITIVE | NOT MADE | 1 | 1.0 |
| 001.jpg | POSITIVE | MADE | 10 | 10.0 |
| 002.jpg | NEGATIVE | MADE | 2 | 2.0 |
| ⋮ | ⋮ | ⋮ | ⋮ | ⋮ |

FIG. 15

| FIRST LEARNING DATA SET ||||| 
|---|---|---|---|---|
| DATA ID | IMAGE | CORRECT ANSWER | CORRECTION | WEIGHT |
| PL000 | IM_P0 | POSITIVE | NOT MADE | 1.0 |
| PL001 | IM_P1 | POSITIVE | NOT MADE | 1.0 |
| PL002 | IM_P2 | NEGATIVE | NOT MADE | 1.0 |
| PL003 | IM_P3 | POSITIVE | NOT MADE | 1.0 |
| ⋮ | ⋮ | ⋮ | ⋮ | ⋮ |

| LEARNING DATA SET OF RARE CASE ||||| 
|---|---|---|---|---|
| DATA ID | IMAGE | CORRECT ANSWER | CORRECTION | WEIGHT |
| AL000 | IM_A0 | POSITIVE | MADE | 5.0 |
| AL001 | IM_A1 | NEGATIVE | MADE | 2.0 |
| AL002 | IM_A2 | POSITIVE | MADE | 5.0 |
| AL003 | IM_A3 | POSITIVE | MADE | 5.0 |
| ⋮ | ⋮ | ⋮ | ⋮ | ⋮ |

DATA PROCESSING APPARATUS AND METHOD, RECOGNITION APPARATUS, LEARNING DATA STORAGE APPARATUS, MACHINE LEARNING APPARATUS, AND PROGRAM

CROSS-REFERENCE TO RELATED APPLICATIONS

The present application is a Continuation of PCT International Application No. PCT/JP2018/046747 filed on Dec. 19, 2018 claiming priority under 35 U.S.C § 119(a) to Japanese Patent Application No. 2018-013764 filed on Jan. 30, 2018. Each of the above applications is hereby expressly incorporated by reference, in its entirety, into the present application.

BACKGROUND OF THE INVENTION

1. Field of the Invention

The present invention relates to a data processing apparatus and a method, a recognition apparatus, a learning data storage apparatus, a machine learning apparatus, and a program and relates to a recognition processing technology using machine learning.

2. Description of the Related Art

The importance of medical image diagnosis such as endoscopic diagnosis, ultrasound diagnosis, X-ray image diagnosis, and computerized tomography (CT) image diagnosis is high at medical sites. Automation of the medical image diagnosis uses image recognition techniques using machine learning. JP1991-102477A (JP-H3-102477A) discloses a radiation image processing apparatus that recognizes an abnormal shadow of a tumor or the like from a radiation image such as a chest X-ray image. The radiation image processing apparatus disclosed in JP1991-102477A (JP-H3-102477A) comprises a configuration that performs relearning for correcting data processing based on an implemented neural network. In a case where a recognition result is not appropriate, the relearning is performed using the image.

A medical use image diagnosis apparatus disclosed in JP1992-090076A (JP-H4-090076A) comprises a learning mechanism that changes a weight coefficient of a node between each unit of a pattern recognition mechanism. A learning method disclosed in JP2017-162098A includes learning an image classification by preparing a plurality of feature extractors, calculating feature amounts from a focused region and a non-focused region using the feature extractors, and weighting the calculated feature amounts. The "medical use image" has the same meaning as a "medical image".

A learning apparatus disclosed in JP2016-006617A prepares a plurality of weight parameters of a hierarchical neural network and performs learning by employing a weight having the least error. A learning apparatus disclosed in JP2005-339322A determines a correct answer or an incorrect answer of an output layer and, in the case of the incorrect answer, calculates the value of normalized exponentiation of a differential coefficient of a response function of the output layer. In the case of error backpropagation, learning is performed using a derivative of the response function that is corrected using the value of normalized exponentiation of the differential coefficient of the response function of the output layer. The term "learning apparatus" may be understood as a term corresponding to a "machine learning apparatus" in the present specification.

SUMMARY OF THE INVENTION

In the medical field, clinical cases that are difficult to recognize are present. Targets that are difficult to recognize are generally rare cases having a small number of clinical cases or the like. Studies for recognizing a lesion or the like using machine learning have been performed. For example, a technology for classifying the lesion as "cancer" or "non-cancer" is considered.

In a case where the lesion is a rare case, the number of samples (number of data) is small, and there is a possibility that the lesion cannot be sufficiently learned in machine learning.

The present invention is conceived in view of such a matter, and an object thereof is to provide a data processing apparatus and a method, a recognition apparatus, a learning data storage apparatus, a machine learning apparatus, and a program capable of improving recognition accuracy for data of a rare case.

In order to achieve the object, the following invention aspects are provided.

A data processing apparatus according to Aspect 1 is a data processing apparatus comprising a data acquisition unit that acquires processing target data, a recognition unit that learns using a learning data set, receives an input of the data acquired through the data acquisition unit, and outputs a recognition result for the data, a recognition result correction unit that corrects the recognition result of the recognition unit in accordance with an instruction from a user, and a machine learning unit that performs learning of the recognition unit using the data in which the recognition result is corrected by the recognition result correction unit, in which the machine learning unit performs learning of the recognition unit by setting a degree of contribution to learning from the data in which the recognition result is corrected to be higher than a degree of contribution to learning of the recognition unit from learning data included in the learning data set.

There is a high possibility that the data in which the user corrects the recognition result of the recognition unit is data of a rare case for which recognition performance in the recognition unit is not sufficient. According to Aspect 1, additional learning of improving the recognition performance of the recognition unit is performed using the data in which the recognition result is corrected by the instruction from the user. At this point, "weighting" is performed such that the degree of contribution from the data in which the recognition result is corrected is set to be relatively higher than from the learning data of the learning data set used in preliminary learning. Accordingly, the recognition performance of the recognition unit for the data of the rare case for which sufficient recognition accuracy is not obtained by only the preliminary learning is preferentially improved, and the recognition accuracy for the data of the rare case is improved.

The data processing apparatus may be configured as a single apparatus or may be configured by combining a plurality of apparatuses. For example, the data processing apparatus may be implemented using one or a plurality of computers. The "apparatus" includes the concept of a "system". The "data" includes the concept of a "signal" and "information". The term "recognition" includes the concepts of identification, determination, inference, estimation, detection, region extraction, and the like.

Aspect 2 is a data processing apparatus in which in the data processing apparatus of Aspect 1, the data acquired by the data acquisition unit is an image, and the recognition unit is used as an image processing apparatus that is an image recognition unit performing a task of image recognition.

The term "image" includes the meaning of "image data". The task of image recognition may include various tasks such as image classification, extraction of a specific region, segmentation, or extraction of a feature of a target object, or an appropriate combination thereof. The term "extraction" includes the concept of "detection".

Aspect 3 is a data processing apparatus in which in the data processing apparatus of Aspect 2, the image is a medical image. The data processing apparatus of Aspect 3 is used as a medical image processing apparatus.

The "medical image" may include various types of images such as an endoscope image, a CT image, an X-ray image, an ultrasound diagnostic image, a magnetic resonance imaging (MRI) image, a positron emission tomography (PET) image, a single photon emission computed tomography (SPECT) image, or a fundus image.

Aspect 4 is a data processing apparatus in which in the data processing apparatus of any one aspect of Aspect 1 to Aspect 3, each of the recognition unit and the machine learning unit is configured using a convolutional neural network.

Aspect 5 is a data processing apparatus in which the data processing apparatus of any one aspect of Aspect 1 to Aspect 4 further comprises a learning data storage unit that stores learning data including the data in which the recognition result is corrected by the recognition result correction unit, and a supervisory signal corresponding to the data.

Here, "store" includes the meaning of "store" in a storage apparatus. According to Aspect 5, the data of the rare case can be collected and accumulated as the learning data. Accordingly, a learning data set useful for improving the recognition performance for the rare case can be obtained.

Aspect 6 is a data processing apparatus in which in the data processing apparatus of Aspect 5, contribution degree information indicating the degree of contribution in a case of being used in learning is assigned to the learning data stored in the learning data storage unit.

It is preferable that the learning data storage unit stores the learning data together with the contribution degree information by associating each learning data with the contribution degree information indicating the degree of contribution in the case of using the learning data in learning. Here, "association" of information is also expressed as "linking".

Aspect 7 is a data processing apparatus in which in the data processing apparatus of Aspect 5 or Aspect 6, the learning data set used in learning of the recognition unit is stored in the learning data storage unit.

It is preferable that an aggregate of all learning data to be used in learning of the recognition unit is stored in the learning data storage unit. The learning data set used in the preliminary learning may also be used in the case of learning for increasing the recognition performance for the rare case. It is preferable that not only the learning data newly collected through correction performed by the recognition result correction unit but also the learning data set used in the preliminary learning are stored in the learning data storage unit.

Aspect 8 is a data processing apparatus in which in the data processing apparatus of any one aspect of Aspect 1 to Aspect 7, the machine learning unit evaluates an error between a recognition result signal indicating the recognition result of the recognition unit and a supervisory signal and updates a parameter of the recognition unit based on the error.

Aspect 9 is a data processing apparatus in which in the data processing apparatus of Aspect 8, the degree of contribution is represented by an error weight coefficient by which the error is multiplied.

By relatively increasing the error weight coefficient, the degree of contribution to the recognition performance from the learning data can be increased. The error weight coefficient is one aspect of the contribution degree information.

Aspect 10 is a data processing apparatus in which in the data processing apparatus of any one aspect of Aspect 1 to Aspect 8, the degree of contribution is represented by the number of times of use of the learning data in learning.

By relatively increasing the number of times of use of the same learning data in learning, the degree of contribution to the recognition performance from the learning data can be increased. The number of times of use in learning is one aspect of the contribution degree information.

Aspect 11 is a data processing apparatus in which the data processing apparatus of any one aspect of Aspect 1 to Aspect 10 further comprises a contribution degree setting unit that sets the degree of contribution in a case of being used in learning for the data in which the recognition result is corrected by the recognition result correction unit.

The degree of contribution can be configured to be set based on a correction result of the recognition result correction unit. In addition, the degree of contribution may be set based on information input from the user.

Aspect 12 is a data processing apparatus in which in the data processing apparatus of Aspect 11, the contribution degree setting unit sets the degree of contribution depending on a category of a correction result of the recognition result correction unit based on the instruction from the user.

For example, the contribution degree setting unit differently sets the degree of contribution between a case where the recognition result corrected by the recognition result correction unit falls in a category "false negative" and a case where the recognition result falls in a category "false positive". It is preferable that the "degree of contribution" for data in which the recognition result of "false negative" is corrected is set to be higher than for data in which the recognition result of "false positive" is corrected.

Aspect 13 is a data processing apparatus in which in the data processing apparatus of Aspect 11, the contribution degree setting unit variably sets the degree of contribution depending on an input from the user.

According to Aspect 13, the user can determine importance or the like of data, and the "degree of contribution" can be appropriately set by reflecting an intention of the user.

Aspect 14 is a data processing apparatus in which in the data processing apparatus of Aspect 13, the recognition result correction unit receives an input of information indicating at least one of severity or rarity of the data in which the recognition result is corrected, and the contribution degree setting unit stepwise sets the degree of contribution depending on at least one of the severity or the rarity input through the recognition result correction unit.

A recognition apparatus according to Aspect 15 comprises a data acquisition unit that acquires processing target data, a recognition unit that learns using a learning data set, receives an input of the data acquired through the data acquisition unit, and outputs a recognition result for the data, and a recognition result correction unit that corrects the recognition result of the recognition unit in accordance with an instruction from a user, in which the recognition result correction unit generates learning data for additional learning including the data in which the recognition result is corrected and a supervisory signal corresponding to the data, and generates correction information indicating that the recognition result is corrected for the data in which the recognition result is corrected.

According to Aspect 15, the data (that is, the data of the rare case) in which the user corrects the recognition result of the recognition unit can be efficiently collected as the learning data for the additional learning. The "additional learning" means learning additionally performed for updating the recognition performance of the recognition unit acquired by the preliminary learning and includes the concept of "relearning".

Aspect 16 is a recognition apparatus in which in the recognition apparatus of Aspect 15, the recognition result correction unit generates contribution degree information indicating a degree of contribution to learning of the recognition unit in a case of using the data in which the recognition result is corrected in learning.

The contribution degree information may be, for example, the error weight coefficient or the number of times of use in learning. The contribution degree information may be understood as one aspect of the correction information.

Aspect 17 is a recognition apparatus in which the recognition apparatus of Aspect 15 or Aspect 16 further comprises a learning data storage unit that stores the learning data and the correction information generated by the recognition result correction unit.

According to Aspect 17, the learning data of the rare case is accumulated in the learning data storage unit through recognition processing of the recognition apparatus and the input of correction of the recognition result from the user. Accordingly, an aggregate of learning data useful for updating the recognition performance of the recognition unit can be obtained.

A learning data storage apparatus according to Aspect 18 is a learning data storage apparatus storing the learning data and the correction information generated by the recognition apparatus of Aspect 15 or Aspect 16.

The learning data storage apparatus may be a storage apparatus functioning as the learning data storage unit in the recognition apparatus or may be a storage apparatus installed outside the recognition apparatus. For example, the learning data storage apparatus may be a data storage server connected to a network or a cloud storage.

Aspect 19 is a learning data storage apparatus in which in the learning data storage apparatus of Aspect 18, an aggregate of the learning data having a data structure including the data in which the recognition result is corrected, the supervisory signal corresponding to the data in which the recognition result is corrected, and contribution degree information indicating a degree of contribution to learning of the recognition unit in a case of using the data in which the recognition result is corrected in learning is stored.

The learning data stored in the learning data storage apparatus has a data structure in which input data is associated with the supervisory signal and the contribution degree information corresponding to the input data.

Aspect 20 is a learning data storage apparatus in which in the learning data storage apparatus of Aspect 19, the data structure further includes information on at least one of severity of a lesion or rarity of a clinical case.

The learning data stored in the learning data storage apparatus can be configured to have a data structure in which information about the severity and/or the rarity is associated in addition to the input data and the supervisory signal and the contribution degree information corresponding to the input data.

A machine learning apparatus according to Aspect 21 is a machine learning apparatus that generates a parameter of a recognition model using the learning data generated by the recognition apparatus of Aspect 15 or Aspect 16, in which the machine learning apparatus performs learning of the recognition model by setting a degree of contribution to learning from the data in which the recognition result is corrected to be higher than a degree of contribution to learning of the recognition model from learning data included in the learning data set.

The "recognition model" is a learned model that acquires tentative recognition performance by machine learning. The recognition model may be understood as a program module performing the recognition processing. The recognition model includes the concepts of a "recognizer", an "identifier", a "discriminator", or a "detector".

The machine learning apparatus of Aspect 21 may be the machine learning unit constituting the data processing apparatus of Aspect 1 or may be an independent apparatus communicably connected to the recognition apparatus of any one aspect of Aspect 15 to Aspect 17. In addition, the machine learning apparatus of Aspect 21 may be communicably connected to the learning data storage apparatus of any one aspect of Aspect 18 to Aspect 20. Here, "connection" includes the concept of connection through an electric communication line (network). The "connection" includes the concepts of both wired connection and wireless connection.

A data processing method according to Aspect 22 is a data processing method comprising a data acquisition step of acquiring processing target data, a recognition step of receiving an input of the data acquired in the data acquisition step and outputting a recognition result for the data, using a recognition model that learns using a learning data set, a recognition result correction step of correcting the recognition result in the recognition step in accordance with an instruction from a user, and a machine learning step of performing learning of the recognition model using the data in which the recognition result is corrected in the recognition result correction step, in which in the machine learning step, learning of the recognition model is performed by setting a degree of contribution to learning from the data in which the recognition result is corrected to be higher than a degree of contribution to learning of the recognition model from learning data included in the learning data set.

In the data processing method of Aspect 22, the same matters as the matters specified in Aspect 2 to Aspect 21 can be appropriately combined. In that case, an element of a processing unit or a function unit as a unit performing processing or an operation specified in the data processing apparatus, the recognition apparatus, or the learning data storage apparatus can be perceived as an element of a step of the corresponding processing or operation. In addition, the data processing method of Aspect 22 may be understood as a method of operating the data processing apparatus.

A program according to Aspect 23 is a program causing a computer to execute a data acquisition step of acquiring processing target data, a recognition step of receiving an input of the data acquired in the data acquisition step and outputting a recognition result for the data, using a recognition model that learns using a learning data set, a recognition result correction step of correcting the recognition result in the recognition step in accordance with an instruction from a user, and a machine learning step of performing learning of the recognition model using the data in which the recognition result is corrected in the recognition result correction step, in which in the machine learning step, learning of the recognition model is performed by setting a degree of contribution to learning from the data in which the recognition result is corrected to be higher than a degree of contribution to learning of the recognition model from learning data included in the learning data set.

In the program of Aspect 23, the same matters as the matters specified in Aspect 2 to Aspect 21 can be appropriately combined. In that case, an element of a processing unit or a function unit as a unit performing processing or an operation specified in the data processing apparatus, the recognition apparatus, or the learning data storage apparatus can be perceived as a program element implementing a step or a function of the corresponding processing or operation.

A data processing apparatus according to another aspect of the present invention is a data processing apparatus including at least one processor that is a processor performing processing of acquiring processing target data, recognition processing of receiving an input of the acquired data and outputting a recognition result for the data using a recognition model that learns using a learning data set, processing of correcting the recognition result of the recognition processing in accordance with an instruction from a user, and machine learning processing of performing learning of the recognition model using data in which the recognition result is corrected, in which the machine learning processing performs learning of the recognition model by setting a degree of contribution to learning from the data in which the recognition result is corrected to be higher than a degree of contribution to learning of the recognition model from learning data included in the learning data set.

A recognition apparatus according to another aspect of the present invention is a data processing apparatus including at least one processor that is a processor performing processing of acquiring processing target data, recognition processing of receiving an input of the acquired data and outputting a recognition result for the data using a recognition model that learns using a learning data set, and processing of correcting the recognition result of the recognition processing in accordance with an instruction from a user, in which the processor further performs processing of generating learning data for additional learning including data in which the recognition result is corrected and a supervisory signal corresponding to the data, and generating correction information indicating that the recognition result is corrected for the data in which the recognition result is corrected.

A recognition apparatus according to another aspect of the present invention is a data processing apparatus including at least one processor that is a processor performing processing of acquiring processing target data, recognition processing of receiving an input of the acquired data and outputting a recognition result for the data using a recognition model that learns using a learning data set, and processing of correcting the recognition result of the recognition processing in accordance with an instruction from a user, in which the processor further performs processing of generating learning data for additional learning including data in which the recognition result is corrected and a supervisory signal corresponding to the data, and generating correction information indicating that the recognition result is corrected for the data in which the recognition result is corrected.

According to the present invention, learning data effective for learning of the rare case can be generated based on a correction instruction for the recognition result from the user. In addition, by performing the additional learning by relatively increasing the degree of contribution to learning for the generated learning data, the recognition accuracy for the data of the rare case can be improved.

BRIEF DESCRIPTION OF THE DRAWINGS

FIG. 2 is a conceptual diagram of a learning data set stored in a learning image storage unit in the first embodiment.

FIG. 6 is a conceptual diagram of a learning data set stored in a learning image storage unit in the second embodiment.

FIG. 8 is a conceptual diagram of a learning data set stored in a learning image storage unit in the third embodiment.

FIG. 15 is a conceptual diagram illustrating an example of an aggregate of learning data stored in the learning image storage unit.

DESCRIPTION OF THE PREFERRED EMBODIMENTS

Figure 1:
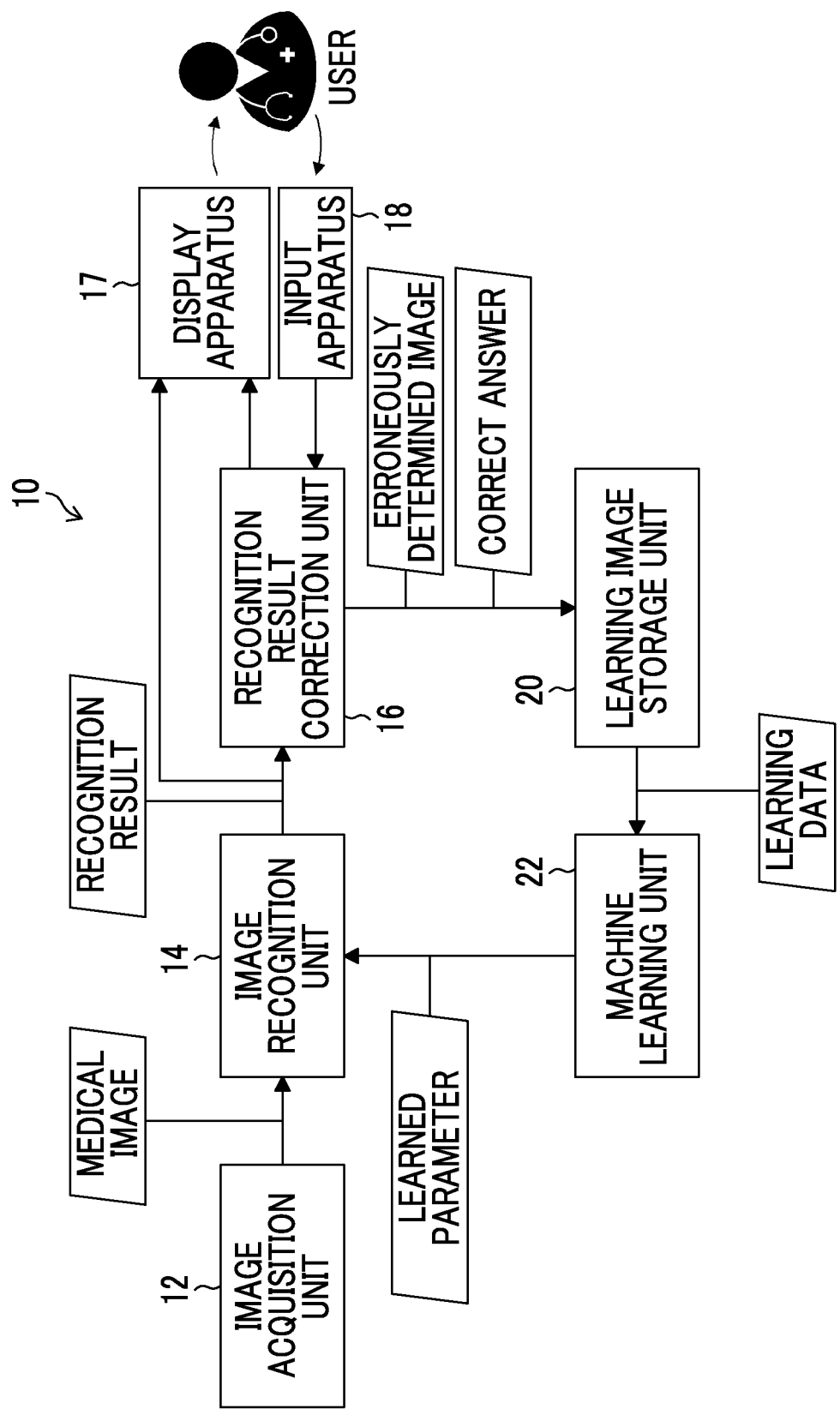
FIG. 1 is a block diagram illustrating functions of an image system according to a first embodiment.

Hereinafter, preferred embodiments of the present invention will be described in detail in accordance with the appended drawings.

<Summary of Image Recognition Using Machine Learning>

Image recognition using machine learning is implemented by "supervised learning" in which a parameter of a recognizer is repeatedly corrected to derive the same recognition result as a supervisory signal provided by a user.

In a case where the recognizer created by machine learning is denoted by f(w, x), an i-th input image is denoted by xi, and a recognition result signal of xi is denoted by yi, $$yi = f(w, xi)$$

is established. Here, w is the parameter of the recognizer. In addition, each of w and x is a vector. In the case of the supervised learning, an error Ei(w, xi) between a supervisory signal ti provided for the i-th input image and the recognition result signal yi is calculated, and E(w) is defined as the sum of the error Ei(w, xi) for n images used in learning.

$$E(w) = \sum_{i=1}^{n} Ei(w, xi)$$ [Expression (1)]

The following expression is one example of Ei(w, xi).

$$Ei(w,xi) = \tfrac{1}{2}\|ti-yi\|^2 = \tfrac{1}{2}\|ti-f(w,xi)\|^2$$ [Expression (2)]

The above expression may be employed as one example of Ei(w, xi).

E(w) is a function of w. Thus, a stabilized global minimum is obtained by sequentially correcting w using the gradient descent method or the like, and the recognizer is optimized. Accordingly, the recognizer derives a recognition result asymptotic to the supervisory signal.

<Object>

However, in a case where data of a rare case is input into the recognizer, there is a possibility that correct recognition is not performed. The reason is that generally, the number of data of the rare case is relatively small in learning data, and learning is insufficient. Data of a case that causes a "recognition error" in the recognizer corresponds to the data of the rare case. The "recognition error" may also be referred to as an "inference error" or an "erroneous determination".

In order to improve recognition accuracy for the rare case in the recognizer, increasing the ratio of the data of the rare case in the learning data is considered. However, in actuality, it is difficult to collect a large amount of data of the rare case. The "learning data" is data for learning in which an input signal used in learning is associated with a supervisory signal indicating a correct answer label corresponding to the input signal, and is also called "training data".

<Summary of Image System According to Embodiment of Present Invention>

An image system according to an embodiment of the present invention automatically collects learning data of a rare case by assigning a correct answer label to data of a case in which an error has occurred in a recognition result using a recognizer. In addition, in the case of performing additional learning of the recognizer using the collected learning data of the rare case, the image system according to the present embodiment performs learning of the recognizer by relatively prioritizing the learning data of the rare case over (ordinary) learning data of other than the rare case and setting a degree of contribution to learning from the learning data of the rare case to be higher than the degree of contribution to learning from the learning data of other than the rare case.

For example, the "learning data of other than the rare case" is learning data included in a learning data set used in learning that is performed for causing the recognizer to acquire necessary initial recognition performance in advance. The "degree of contribution to learning from the learning data" refers to a degree to which the learning data contributes to learning performed for causing the recognizer to acquire the recognition performance. The degree to which the learning data contributes to learning may be understood as a degree to which the learning data contributes to the recognition performance acquired by the recognizer by learning. The degree to which the learning data contributes to learning may also be referred to as a contribution degree to learning or a contribution degree of the learning data to the recognition performance and may be understood as a "weight" of each learning data in learning. For example, the contribution degree of the learning data for the recognition performance is reflected on a loss function used in evaluation of an error in error backpropagation (backpropagation).

In the image system according to the present embodiment, weighting is performed such that the contribution degree of the error Ei(w, xi) for learning in data of a case in which an error has occurred in the recognition result using the recognizer is set to be relatively higher than the contribution degree of Ei(w, xi) for learning obtained from other learning data.

A form of using an error weight coefficient ai by which the error Ei(w, xi) is multiplied may be employed as one of specific methods of performing the weighting by setting the degree of contribution to the recognition performance for the learning data of the rare case to be relatively high.

For example, in a case where an error occurs in the recognition result of a certain image xi and a correction instruction is input from the user for the erroneous recognition result, minimized E(w) is the following expression in a case where the error weight coefficient decided based on a correction result for the image xi is denoted by ai.

$$E(w) = \sum_{i=1}^{n} ai \cdot Ei(w, xi)$$ [Expression (3)]

The above expression represents minimized E(w).

The error weight coefficient for the learning data of other than the rare case is set to a standard value (for example, "1.0"). The error weight coefficient for the learning data of the rare case is set to a value (for example, "2.0") greater than the standard value.

Accordingly, the recognizer acquires high recognition performance for the data of the rare case. The reason is that optimization of the parameter of the recognizer is preferentially performed for data in which a weighted error represented by "ai·EI(w, xi)" is large.

<Configuration of Image System According to First Embodiment>

FIG. 1 is a block diagram illustrating functions of an image system according to a first embodiment. An image system 10 is a data processing system handling a medical image and comprises an image acquisition unit 12, an image recognition unit 14, a recognition result correction unit 16, a learning image storage unit 20, and a machine learning unit 22. In addition, the image system 10 comprises a display apparatus 17 and an input apparatus 18 as a user interface.

The image system 10 of the present example performs analysis of an image (image recognition), collection of images, machine learning for recognition processing, and the like. The image system 10 may be configured as one data processing apparatus or may be configured by combining a plurality of apparatuses. For example, the image system 10 can be implemented using one or a plurality of computers. The image system 10 is one example of the "data processing apparatus" and functions as an image processing apparatus. The image system 10 can be used as a diagnosis assistance apparatus that assists medical examination, treatment, diagnosis, or the like performed by a doctor or the like. The term "diagnosis assistance" includes the concept of medical examination assistance and/or treatment assistance.

The image acquisition unit 12 is an interface for acquiring a processing target image. For example, the image acquisition unit 12 may be a connector terminal to which a video connector of an electronic endoscope, not illustrated, is connected, or may be a signal input terminal of an image processing circuit. Alternatively, the image acquisition unit 12 may be a communication network terminal, a media interface terminal for external storage media, or a connection terminal for an external apparatus, or an appropriate combination thereof. The image acquisition unit 12 is one example of a "data acquisition unit". A medical image acquired through the image acquisition unit 12 is one example of "processing target data".

The image acquisition unit 12 may include an image generation apparatus that generates the processing target image. The image generation apparatus may be one or a combination of various medical apparatuses (image examination apparatuses) such as an electronic endoscope apparatus, a CT apparatus, an X-ray diagnosis apparatus, an ultrasound diagnostic apparatus, an MRI apparatus, a nuclear medicine diagnosis apparatus, or a fundus camera.

The image recognition unit 14 includes a recognizer that learns by machine learning. The recognizer is a learned model that acquires recognition performance by machine learning. The learned model that performs the recognition processing is referred to as a "recognition model". For example, the recognizer can be configured using a convolutional neural network (CNN). Learning performed for acquiring the initial recognition performance as the recognition model is referred to as "first learning". A learning data set used in the first learning of the recognizer is referred to as a "first learning data set". The first learning data set may be a learning data set that is prepared in advance. The first learning may be performed using the machine learning unit 22 or may be performed using a separate machine learning apparatus, not illustrated. In the first learning, the contribution degree to learning from each learning data used in learning is constant (non-weighted). The first learning may also be referred to as "non-weighted learning".

The image recognition unit 14 receives an input of the image acquired through the image acquisition unit 12 and outputs a recognition result for the image. For example, the image recognition unit 14 performs processing of at least one of extraction of a feature amount from the image, classification of the image, detection of a focused region, segmentation, or calculation of a similarity. Here, a recognition task of binary classification of determining "cancer" (positive) or "non-cancer" (negative) will be illustrated as a simple example. The recognition result of the image recognition unit 14 is displayed on the display apparatus 17. The image recognition unit 14 is one example of a "recognition unit".

The display apparatus 17 may be, for example, a liquid crystal display, an organic electro-luminescence (EL) (OEL) display, or a projector, or an appropriate combination thereof. Besides the recognition result, the display apparatus 17 may display the processing target image and various information such as various setting information necessary for processing.

The input apparatus 18 may be, for example, an operation button or a keyboard, a mouse, a touch panel, or a voice input apparatus, or an appropriate combination thereof. The user can input various instructions by operating the input apparatus 18. The user can inspect the recognition result and the image displayed on the display apparatus 17 and can provide an instruction to correct the recognition result from the input apparatus 18 in a case where it is determined that the recognition result is "false". That is, the user can input information about a "correct answer" for correcting an erroneous recognition result output by the image recognition unit 14 from the input apparatus 18.

The recognition result correction unit 16 performs processing of correcting the recognition result of the image recognition unit 14 in accordance with the instruction from the user. Data corrected by the recognition result correction unit 16 is assigned a label "correction made" and stored in the learning image storage unit 20. That is, the recognition result correction unit 16 transmits data including an "erroneously determined image" erroneously recognized by the image recognition unit 14 and a supervisory signal indicating the "correct answer" provided by the user to the learning image storage unit 20.

The learning image storage unit 20 is a data storage unit that stores learning data including the erroneously determined image which is data in which the recognition result is corrected by the recognition result correction unit 16, and the supervisory signal corresponding to the erroneously determined image. For example, the learning image storage unit 20 is configured to include a hard disk apparatus, an optical disk, a magneto-optical disk, or a semiconductor memory, or a storage apparatus configured using an appropriate combination thereof. The erroneously determined image corresponds to an image of the rare case.

The learning image storage unit 20 also stores the first learning data set. An image used in the first learning is assigned a label "correction not made" and stored in the learning image storage unit 20. The learning image storage unit 20 may also store data not corrected by the recognition result correction unit 16, that is, data correctly recognized by the image recognition unit 14, as additional learning data. The recognition result correction unit 16 can assign the label "correction not made" to the data correctly recognized by the image recognition unit 14 and transmit the data to the learning image storage unit 20. The learning image storage unit 20 is one example of a "learning data storage unit".

The machine learning unit 22 is configured to include the same recognizer for learning as the recognizer of the image recognition unit 14. The machine learning unit 22 performs additional learning of the recognizer using the learning data stored in the learning image storage unit 20. The machine learning unit 22 updates the parameter of the recognizer of the image recognition unit 14 by supplying a parameter of the recognizer obtained by the additional learning to the image recognition unit 14.

In the case of performing the additional learning by the machine learning unit 22 and updating the parameter of the recognizer, the error weight coefficient ai is changed in accordance with the presence or absence of the label "correction made" in the learning data. For example, the error weight coefficient ai in the case of the learning data to which the label "correction made" is assigned is set to "2.0", and the error weight coefficient ai in the case of the learning data to which the label "correction not made" is assigned is set to "1.0".

FIG. 2 is a conceptual diagram of the learning data set stored in the learning image storage unit 20. In the table illustrated in FIG. 2, an image to which a label "made" is assigned in the field of "correction" is data corrected by the recognition result correction unit 16, that is, the erroneously determined image. A part or the entirety of an image to which a label "not made" is assigned in the field of "correction" is data used in the first learning. A numerical value shown in the field of "weight" is the error weight coefficient.

The machine learning unit 22 performs machine learning in accordance with, for example, the minibatch method using the learning data set stored in the learning image storage unit 20.

<Minibatch Learning>

A minibatch is a partial set of a prepared learning data group (learning data set) and is a learning data group configured with a plurality of learning samples selected from the entire prepared learning data group. Minibatch learning is a method of evaluating an error between an output signal and a correct answer (supervisory signal) for each learning sample using all learning samples included in the minibatch and collectively updating the parameter of the recognizer in units of minibatches using an evaluation result of the error.

<Data Processing Method Performed by Image System>

Figure 3:
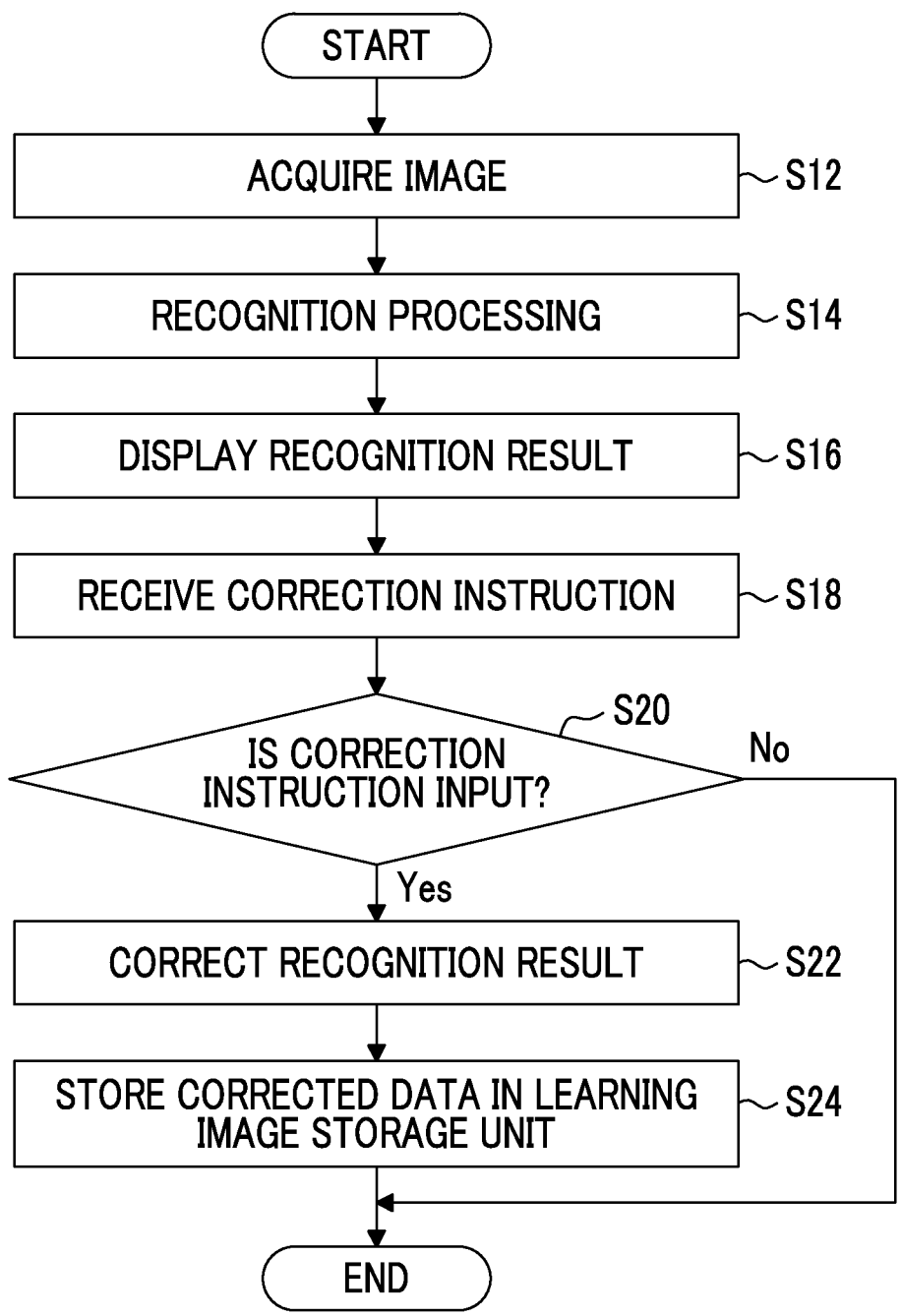
FIG. 3 is a flowchart illustrating an operation of the image system according to the first embodiment.

FIG. 3 is a flowchart illustrating an operation of the image system according to the first embodiment. In step S12, the image acquisition unit 12 acquires the processing target image. Step S12 is one example of a "data acquisition step".

In step S14, the image recognition unit 14 performs the recognition processing on the input image and outputs the recognition result. Step S14 is one example of a "recognition step".

In step S16, the display apparatus 17 displays the recognition result of the image recognition unit 14. For example, in a case where the image recognition unit 14 performs a recognition task of classification into two categories of "cancer" or "non-cancer", the image acquired through the image acquisition unit 12 and text information showing "cancer" or "non-cancer" are displayed on the display apparatus 17.

In step S18, the recognition result correction unit 16 receives the correction instruction from the user. The user determines whether or not the recognition result is correct by checking the image and the recognition result displayed on the display apparatus 17. In a case where the recognition result is erroneous, the user can input the instruction to correct the recognition result using the input apparatus 18. Meanwhile, in a case where the recognition result is correct, the user can input an instruction to approve the recognition result using the input apparatus 18.

In step S20, the recognition result correction unit 16 determines whether or not the correction instruction for the recognition result is input from the user. In a case where the correction instruction is input from the input apparatus 18, a determination result of step S20 results in a "Yes determination". Meanwhile, in a case where the instruction to approve the recognition result is input from the input apparatus 18, the determination result of step S20 results in a "No determination".

In a case where the determination result of step S20 is the "Yes determination", a transition is made to step S22. In step S22, the recognition result correction unit 16 corrects the recognition result in accordance with the instruction from the user. Step S22 corresponds to provision of the correct supervisory signal for the erroneously determined image. Step S22 is one example of a "recognition result correction step".

In step S24, the recognition result correction unit 16 stores data in which the recognition result is corrected in the learning image storage unit 20. After step S24, the flowchart in FIG. 3 is finished.

Meanwhile, in a case where the determination result of step S20 is the "No determination", the flowchart in FIG. 3 is finished by omitting the processing of step S22 and step S24.

In a case where the determination result of step S20 is the "No determination", the data may be assigned the label "correction not made" and stored in the learning image storage unit 20.

The image system 10 can collect the data of the rare case by executing the processing illustrated in the flowchart in FIG. 3.

The procedure described using the flowchart in FIG. 3 is one example of a method of operating the data processing apparatus as a medical image apparatus performing image recognition processing and image collection processing.

<Example of Machine Learning Method>

Figure 4:
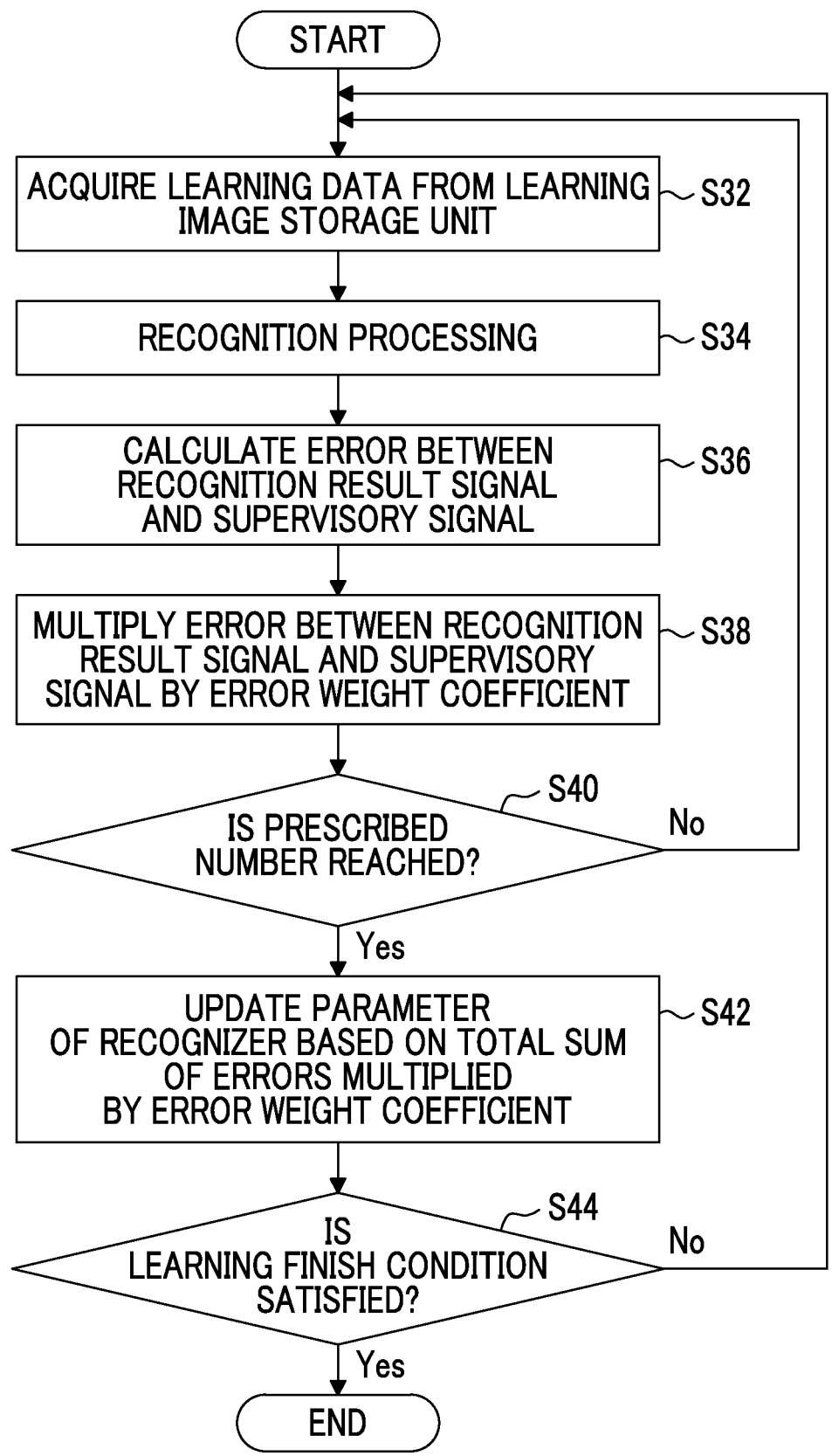
FIG. 4 is a flowchart illustrating one example of a machine learning method performed by a machine learning unit.

FIG. 4 is a flowchart illustrating one example of a machine learning method performed by the machine learning unit. In step S32, the machine learning unit 22 acquires the learning data from the learning image storage unit 20.

In step S34, the recognizer of the machine learning unit 22 performs the recognition processing using the image of the acquired learning data as an input signal and outputs the recognition result.

In step S36, the machine learning unit 22 calculates an error between a recognition result signal output by the recognizer and the supervisory signal. For example, the recognition result signal is a score representing the accuracy of recognition. A determination of "cancer" or "non-cancer" is made based on the score indicated by the recognition result signal. For example, in a case where the accuracy of recognition is represented by a numerical value in the range of "greater than or equal to 0 and less than or equal to 1", the supervisory signal is "0" in the case of non-cancer (negative) and is "1" in the case of cancer (positive).

In step S38, the machine learning unit 22 evaluates the error by multiplying the error calculated in step S36 by the error weight coefficient. An evaluation value of the error calculated in step S38 is called the "weighted error".

In step S40, the machine learning unit 22 determines whether or not the number of images used in learning has reached a prescribed number. For example, the prescribed number is a predetermined number of minibatches. In a case where a determination result of step S40 is the "No determination", the machine learning unit 22 returns to step S32 and acquires the subsequent learning data. The machine learning unit 22 repeats the processing of step S32 to step S40 in units of minibatches.

In a case where the determination result of step S40 is the "Yes determination", the machine learning unit 22 transitions to step S42. In step S42, the machine learning unit 22 updates the parameter of the recognizer based on the total sum of the prescribed number of weighted errors calculated in step S38.

In step S44, the machine learning unit 22 determines whether or not a learning finish condition is satisfied. IN a case where a determination result of step S44 is the "No determination", that is, in a case where it is determined that the learning finish condition is not satisfied, the machine learning unit 22 returns to step S32 and repeats step S32 to step S44 until the learning finish condition is satisfied.

The learning finish condition may be set based on the value of the error or may be set based on the number of updates. As a method based on the value of the error, for example, the learning finish condition may be such that the error falls within a prescribed range. As a method based on the number of updates, for example, the learning finish condition may be such that the number of updates reaches a prescribed number.

An aspect of linearly changing or an aspect of stepwise changing weighting of the loss function used as an evaluation function of the error in accordance with the number of updates may be available.

In a case where the determination result of step S44 is the "Yes determination", the processing of learning is finished by deciding the parameter of the recognizer.

The parameter learned in such a manner is applied to the recognizer of the image recognition unit 14. Accordingly, the recognition accuracy of the image recognition unit 14 for the rare case is improved.

Processing of performing learning of the recognizer by executing steps S32 to S44 illustrated in the flowchart in FIG. 4 is one example of a "machine learning step".

<Modification Example of Flowchart>

The calculation in step S38 may be performed between step S40 and step S42. For example, the calculation corresponding to step S38 may be performed in an evaluation function that collectively evaluates the error in units of minibatches.

<Summary of Image System According to Second Embodiment>

In the first embodiment, an example of using two types of ai=1.0 in the case of "correction not made" and ai=2.0 in the case of "correction made" with respect to the error weight coefficient ai has been illustrated. However, a specific numerical value of the error weight coefficient ai is not limited to this example. In addition, the error weight coefficient ai may be set in multiple stages of more than or equal to three types. For example, the error weight coefficient ai may be variably set in multiple stages of more than or equal to three types depending on the significance of erroneous determination risk, the rarity of a clinical case, or the severity of a lesion, or a combination thereof.

At sites of medical image diagnosis, a bias is present in the recognition performance to be acquired depending on the category of recognition. For example, the risk of determining a positive lesion as being negative (false negative) is higher than the risk of determining a negative lesion as being positive (false positive). Thus, acquisition of the recognition performance that reduces false negative recognition results is required.

In order to deal with such a requirement, in a case where the recognition result of the image recognition unit 14 belongs to a category "false negative", the error weight coefficient set in the case of correcting the recognition result is preferably set to be higher. For example, in a case where the category of the recognition result of data in which the recognition result is corrected is "false negative", ai=5.0 is set. In the case of "false positive", ai=2.0 is set. In the case of "correction not made", ai=1.0 is set.

Figure 5:
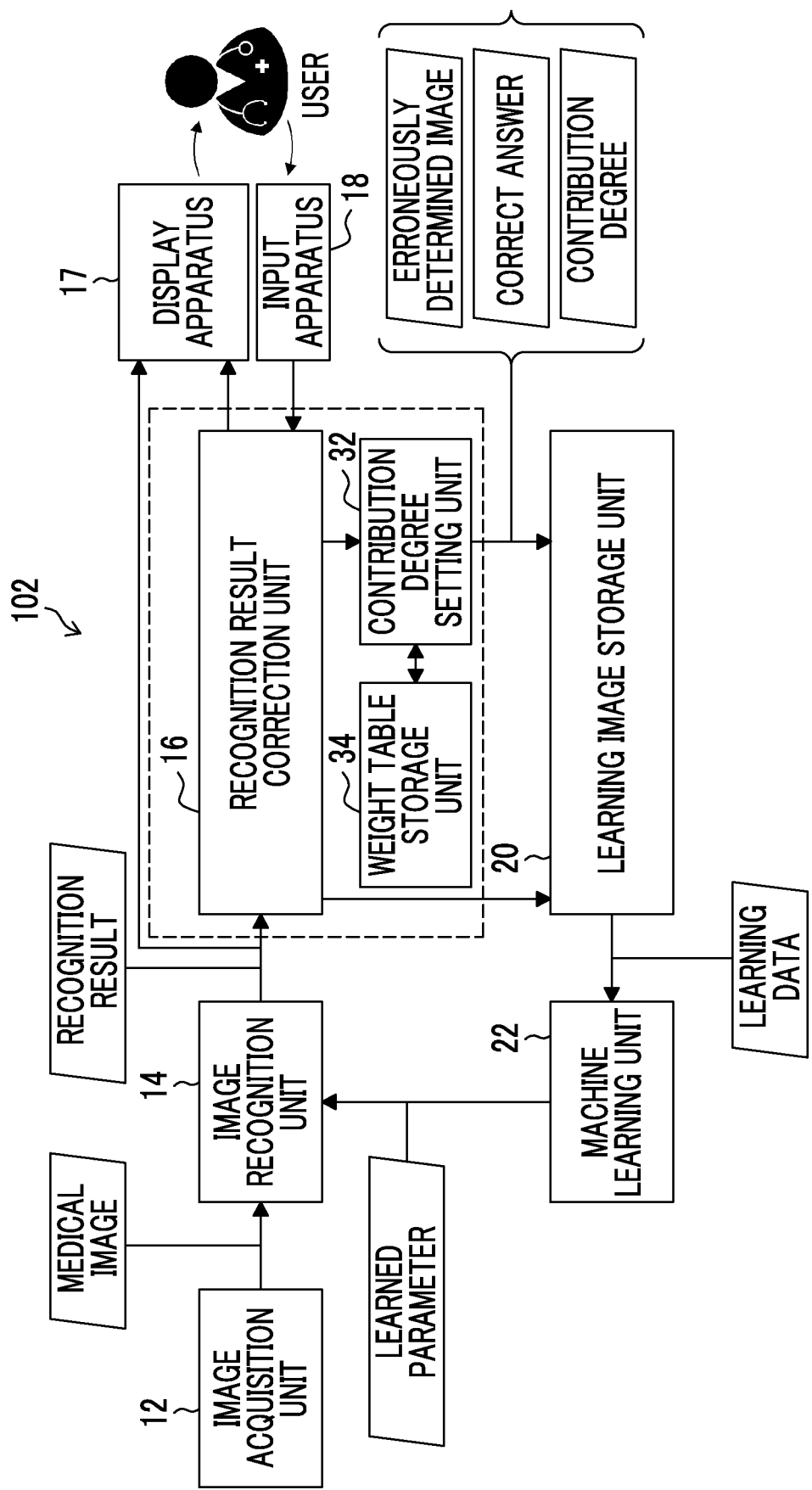
FIG. 5 is a block diagram illustrating functions of an image system according to a second embodiment.

FIG. 5 is a block diagram illustrating functions of an image system according to a second embodiment. In FIG. 5, elements that are the same as or similar to the configuration described with FIG. 1 are designated by the same reference signs, and descriptions of such elements will be omitted. Differences from the first embodiment will be described. An image system 102 according to the second embodiment illustrated in FIG. 5 further comprises a contribution degree setting unit 32 and a weight table storage unit 34 in addition to the configuration of the image system 10 according to the first embodiment. The contribution degree setting unit 32 may be incorporated in the recognition result correction unit 16. In addition, the weight table storage unit 34 may be incorporated in the recognition result correction unit 16.

The contribution degree setting unit 32 is a processing unit that sets the degree of contribution in the case of using data (erroneously determined image) in which the recognition result is corrected by the recognition result correction unit 16 in the additional learning. In the case of the present example, the "degree of contribution" is represented by the error weight coefficient. The "degree of contribution" may be referred to as the "contribution degree". The error weight coefficient is one example of "contribution degree information".

The weight table storage unit 34 is a storage unit storing a weight table in which a correspondence relationship between a correction result of the recognition result correction unit 16 and the error weight coefficient is set. The weight table may be a look-up table that is referred to in order to set an appropriate error weight coefficient from correction information including the correction result of the recognition result correction unit 16.

For example, one example of the weight table in the case of setting the error weight coefficient depending on the category of the correction result such as correction of "false negative", correction of "false positive", or "correction not made" is shown in Table 1 below.

TABLE 1

| Category of Correction Result | Weight |
|---|---|
| False Negative | 5.0 |
| False Positive | 2.0 |
| Correction Not Made | 1.0 |

The contribution degree setting unit 32 sets the error weight coefficient indicating the degree of contribution in the case of using the erroneously determined image in learning by referring to the weight table based on the correction information from the recognition result correction unit 16.

The erroneously determined image in which the recognition result is corrected by the recognition result correction unit 16 is linked (associated) with the error weight coefficient set by the contribution degree setting unit 32 and the correction information and is stored in the learning image storage unit 20.

FIG. 6 is a conceptual diagram of a learning data set stored in the learning image storage unit 20 in the second embodiment. As illustrated in FIG. 6, the learning image storage unit 20 stores an aggregate of learning data in which the input image, information about the correct answer, the correction information, and the weight (error weight coefficient) are associated.

Third Embodiment

At sites of medical image diagnosis, even the same positive lesions have different severity. That is, it is necessary to set higher recognition accuracy for a lesion having high severity.

An image system according to a third embodiment sets the degree of contribution depending on the severity of the lesion. For example, after the recognition result of the image recognition unit 14 is output, the user inspects the output recognition result and the image. In a case where it is determined that the recognition result is false, the user inputs the correction instruction using the input apparatus 18, and the correct answer is provided by the recognition result correction unit 16. The recognition result correction unit 16 assigns the label "correction made" to the erroneously determined image and performs correction in accordance with the instruction from the user. At this point, the user also inputs the severity of the lesion. The image in which the recognition result is corrected is stored in the learning image storage unit 20 together with information input in the recognition result correction unit 16.

The severity input by the user may be divided into levels of a plurality of stages. As the severity input by the user, for example, 10 stages of 1 to 10 may be used, or three stages of severity "low", "medium", and "high" may be used.

In the case of updating the parameter by the machine learning unit 22, the severity is converted into the error weight coefficient and is used in calculation of the loss function. As the severity is increased, the error weight coefficient is set to be increased. For example, in the case of "correction made", ai=(severity of 10 stages)×1.0 is set. In the case of "correction not made", ai=1.0 is set.

Figure 7:
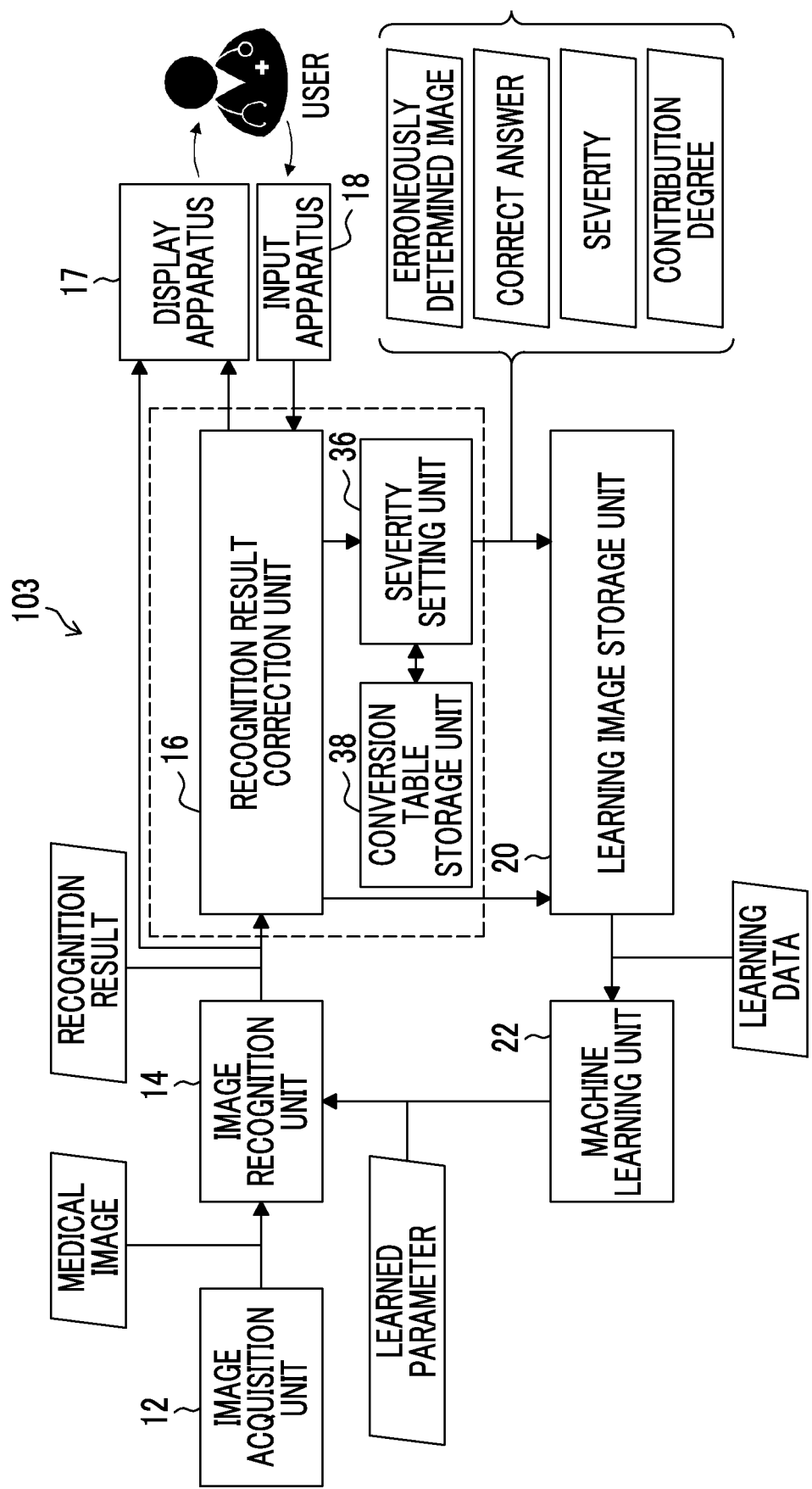
FIG. 7 is a block diagram illustrating functions of an image system according to a third embodiment.

FIG. 7 is a block diagram illustrating functions of the image system according to the third embodiment. In FIG. 7, elements that are the same as or similar to the configuration described with FIG. 1 are designated by the same reference signs, and descriptions of such elements will be omitted. Differences from the first embodiment will be described. An image system 103 according to the third embodiment illustrated in FIG. 7 further comprises a severity setting unit 36 and a conversion table storage unit 38 in addition to the configuration of the image system 10 according to the first embodiment. The severity setting unit 36 may be incorporated in the recognition result correction unit 16. In addition, the conversion table storage unit 38 may be incorporated in the recognition result correction unit 16.

The severity setting unit 36 sets the severity of the lesion based on information input by the user from the input apparatus 18.

The conversion table storage unit 38 is a storage unit storing a conversion table in which a conversion relationship of conversion from the severity into the error weight coefficient is set. The conversion table may be a look-up table in which a correspondence relationship between the severity and the error weight coefficient is specified.

The severity setting unit 36 sets the error weight coefficient corresponding to the severity by referring to the conversion table based on the severity input by the user. The severity setting unit 36 corresponds to one example of a "contribution degree setting unit". The conversion table may be understood as one example of the weight table.

The erroneously determined image in which the recognition result is corrected by the recognition result correction unit 16 is linked with the correction information of the recognition result correction unit 16, the severity input from the user, and the error weight coefficient set in accordance with the severity and is stored in the learning image storage unit 20.

FIG. 8 is a conceptual diagram of a learning data set stored in the learning image storage unit 20 in the third embodiment. In FIG. 8, an example of employing the severity of 10 stages is illustrated. As illustrated in FIG. 8, the learning image storage unit 20 stores an aggregate of learning data in which the input image, information about the correct answer, the correction information, the severity, and the weight (error weight coefficient) are associated.

Fourth Embodiment

Figure 9:
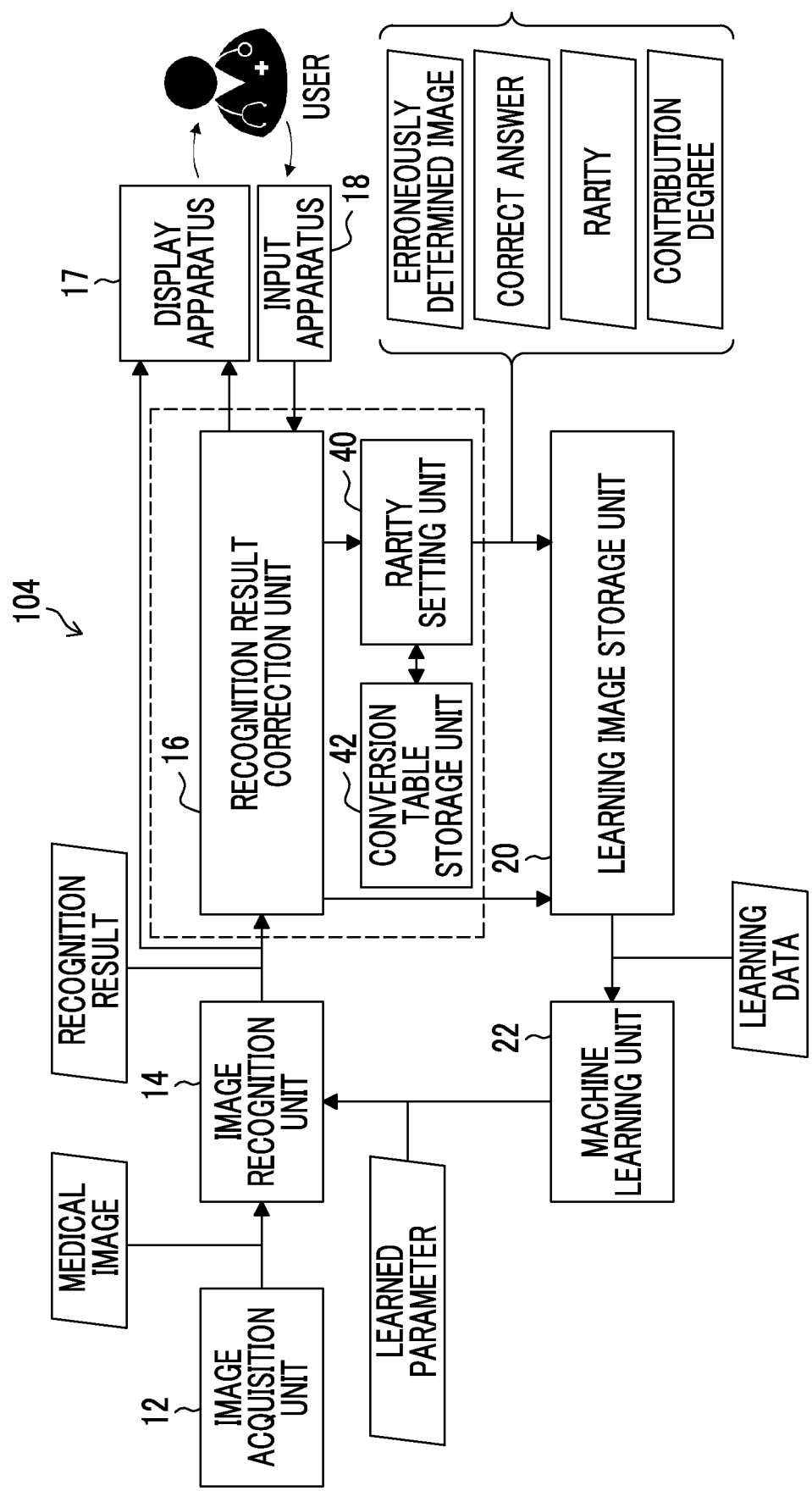
FIG. 9 is a block diagram illustrating functions of an image system according to a fourth embodiment.

Instead of the "severity" described in the third embodiment, the "rarity" of the clinical case may be used. FIG. 9 is a block diagram illustrating functions of an image system according to a fourth embodiment. In FIG. 9, elements that are the same as or similar to the configuration described with FIG. 7 are designated by the same reference signs, and duplicate descriptions will be omitted. Differences from the third embodiment will be described. An image system 104 according to the fourth embodiment illustrated in FIG. 9 comprises a rarity setting unit 40 and a conversion table storage unit 42 instead of the severity setting unit 36 and the conversion table storage unit 38 of the image system 103 according to the third embodiment.

The rarity setting unit 40 may be incorporated in the recognition result correction unit 16. In addition, the conversion table storage unit 42 may be incorporated in the recognition result correction unit 16.

The rarity setting unit 40 sets the rarity of the clinical case based on information input by the user from the input apparatus 18. The conversion table storage unit 42 is a storage unit storing a conversion table in which a correspondence relationship of conversion from the rarity into the error weight coefficient is set. The conversion table may be a look-up table in which a correspondence relationship between the rarity and the error weight coefficient is specified.

In the image system 104, after the recognition result of the image recognition unit 14 is output, the user inspects the output recognition result and the image. In a case where it is determined that the recognition result is false, the user inputs the correction instruction using the input apparatus 18, and the correct answer is provided by the recognition result correction unit 16. The recognition result correction unit 16 assigns the label "correction made" to the erroneously determined image and performs correction in accordance with the instruction from the user. At this point, the user also inputs the rarity of the clinical case. The image in which the recognition result is corrected is stored in the learning image storage unit 20 together with information input in the recognition result correction unit 16.

The rarity input by the user may be divided into levels of a plurality of stages. As the rarity input by the user, for example, 10 stages of 1 to 10 may be used, or three stages of rarity "low", "medium", and "high" may be used.

In the case of updating the parameter by the machine learning unit 22, the rarity is converted into the error weight coefficient and is used in calculation of the loss function. As the rarity is increased, the error weight coefficient is set to be increased. For example, in the case of "correction made", ai=(rarity of 10 stages)×1.0 is set. In the case of "correction not made", ai=1.0 is set.

The learning image storage unit 20 stores an aggregate of learning data in which the input image, information about the correct answer, the correction information, the rarity, and the weight (error weight coefficient) are associated.

Fifth Embodiment

In the case of increasing the recognition performance of the recognizer by machine learning, all images stored as the learning image are basically used in learning. The series of processing for increasing the recognition accuracy by updating the parameter or the like of the recognizer using all learning images is handled as a unit of "one epoch". In a case where the learning method is deep learning or the like, it is rare that target performance is obtained in one epoch, and repetition is generally performed in a few epochs. For the update of the recognizer performed in one epoch, the update is basically performed using all images once. The reason is for equalizing contribution to the recognition performance from each data.

In the fifth embodiment of the present invention, for the image in which the recognition result of the recognizer is corrected by the user, the number of times of use in the update of the recognizer in one epoch is increased. Accordingly, contribution to the recognition performance from the image of "correction made" is increased, and the recognizer is more preferentially optimized for the image of "correction made".

That is, the number of times of use in the update of the parameter of the recognizer in one epoch may be used instead of or in combination with the "error weight coefficient" described thus far. The number of times of use of the same learning data in one epoch corresponds to one example of a numerical value representing the degree of contribution (contribution degree) to the recognition performance. The number of times of use of the learning data is one example of the "contribution degree information".

In the case of controlling the degree of contribution using the number of times of use of the same learning data in one epoch, the evaluation function (loss function) shown in [Expression (1)] can be used instead of the error weight coefficient.

Sixth Embodiment: Construction Example 1 of Image System

As Construction Example 1 of the image system described as each embodiment of the first embodiment to the fifth embodiment, it is considered that all of the image acquisition unit 12, the image recognition unit 14, the recognition result correction unit 16, the learning image storage unit 20, and the machine learning unit 22 are installed at a facility such as a hospital. In this case, for example, a doctor who is the user corrects the recognition result of the image recognition unit 14, and based on the result, the correction result and the image (erroneously determined image) are stored in the learning image storage unit 20. The machine learning unit 22 updates the recognizer of the image recognition unit 14 using the image stored in the learning image storage unit 20.

The image system 10 comprising the image acquisition unit 12, the image recognition unit 14, the recognition result correction unit 16, the learning image storage unit 20, and the machine learning unit 22 is one example of a recognition apparatus having a function of generating and collecting learning data to be used in learning of a rare case, and a learning function.

Seventh Embodiment: Construction Example 2 of System

As another Construction Example 2 of the image system according to the embodiment of the present invention, it is considered that the image acquisition unit 12, the image recognition unit 14, the recognition result correction unit 16, and the learning image storage unit 20 are installed at a facility such as a hospital and the machine learning unit 22 is installed at a remote facility.

Figure 10:
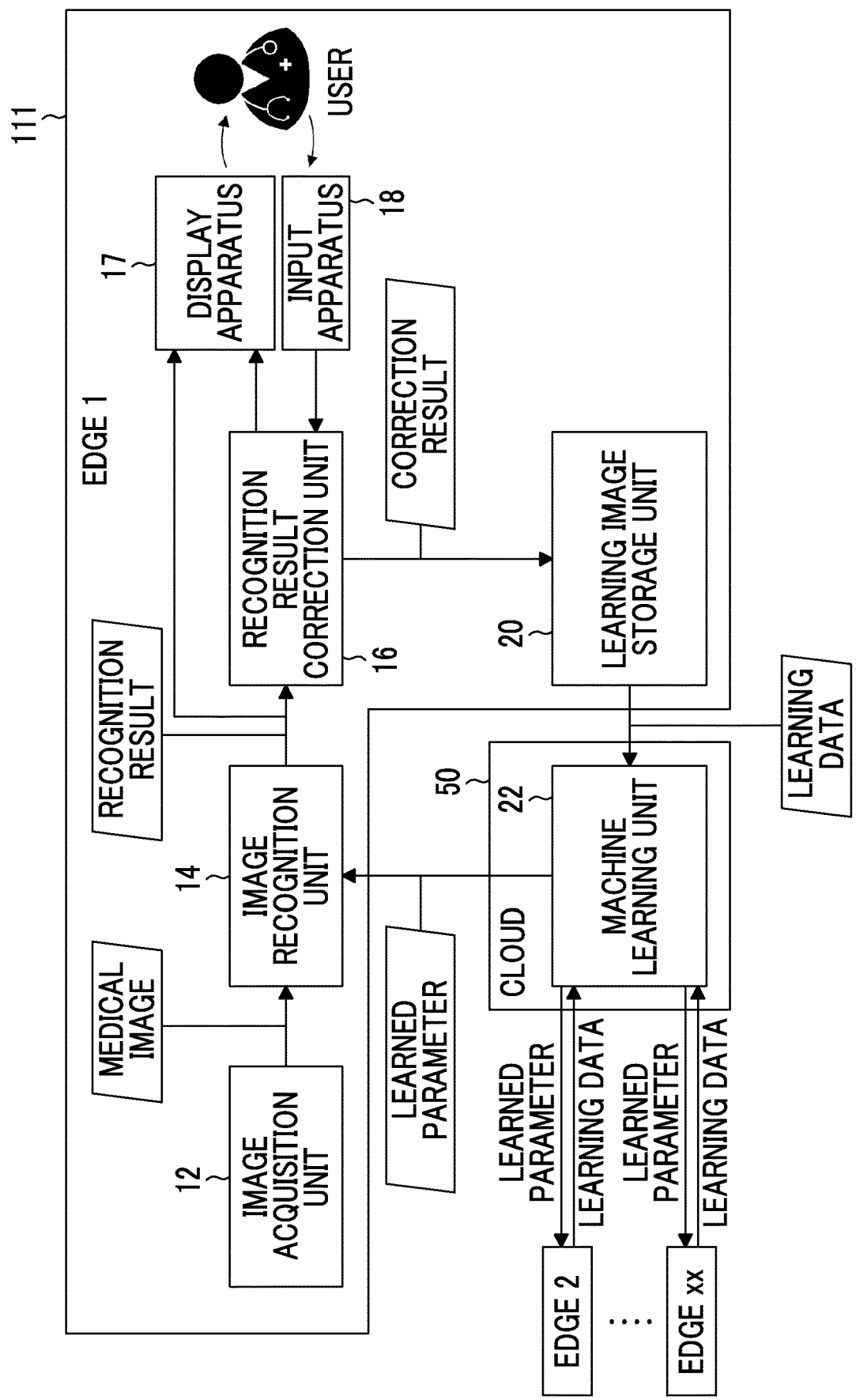
FIG. 10 is a block diagram illustrating a configuration of an image system according to a seventh embodiment.

FIG. 10 is a block diagram illustrating a configuration of an image system according to a seventh embodiment. The facility at which the image acquisition unit 12, the image recognition unit 14, the recognition result correction unit 16, and the learning image storage unit 20 are installed is called an "edge", and the facility at which the machine learning unit 22 is installed is called a "cloud".

The edge is a medical institution such as a hospital. The edge is set as a facility at which medical image diagnosis is performed. A plurality of edges may be present. In FIG. 10, the plurality of edges are denoted by an "edge 1", an "edge 2", . . . , an "edge xx". Each edge will be representatively described as an "edge 111".

Each edge 111 and a cloud 50 are connected through a network. In FIG. 10, illustration of the network is omitted. The "network" has the same meaning as an electric communication line. Data that is accumulated in the learning image storage unit 20 by correcting the recognition result by each user in each edge 111 is transmitted to the cloud 50 through the network. In the cloud 50, learning is performed by the machine learning unit 22 based on the transmitted learning data, and the parameter of the recognizer is updated.

The cloud 50 distributes the updated parameter to the image recognition unit 14 of each edge 111. In FIG. 10, the parameter distributed to each edge 111 from the cloud 50 is denoted by a "learned parameter".

In each edge 111, the parameter of the image recognition unit 14 is updated in accordance with the learned parameter provided from the cloud 50.

In the case of the seventh embodiment illustrated in FIG. 10, the first learning data set is not necessarily stored in the learning image storage unit 20 in each edge 111. For example, the first learning data set may be stored in the cloud 50, and the learning image storage unit 20 of each edge 111 may store only data in which the recognition result is corrected among images newly acquired through the image acquisition unit 12.

Each edge 111 illustrated in FIG. 10 is one example of a recognition apparatus having a function of generating and collecting learning data to be used in learning of a rare case. In addition, the machine learning unit 22 illustrated in FIG. 10 is one example of a "machine learning apparatus" that performs learning using the learning data generated by the recognition apparatus.

Eighth Embodiment: Construction Example 3 of System

As another Construction Example 3 of the image system described as each embodiment of the first embodiment to the fifth embodiment, it is considered that the image acquisition unit 12, the image recognition unit 14, and the recognition result correction unit 16 are installed at a facility such as a hospital and the learning image storage unit 20 and the machine learning unit 22 are installed at a remote facility.

Figure 11:
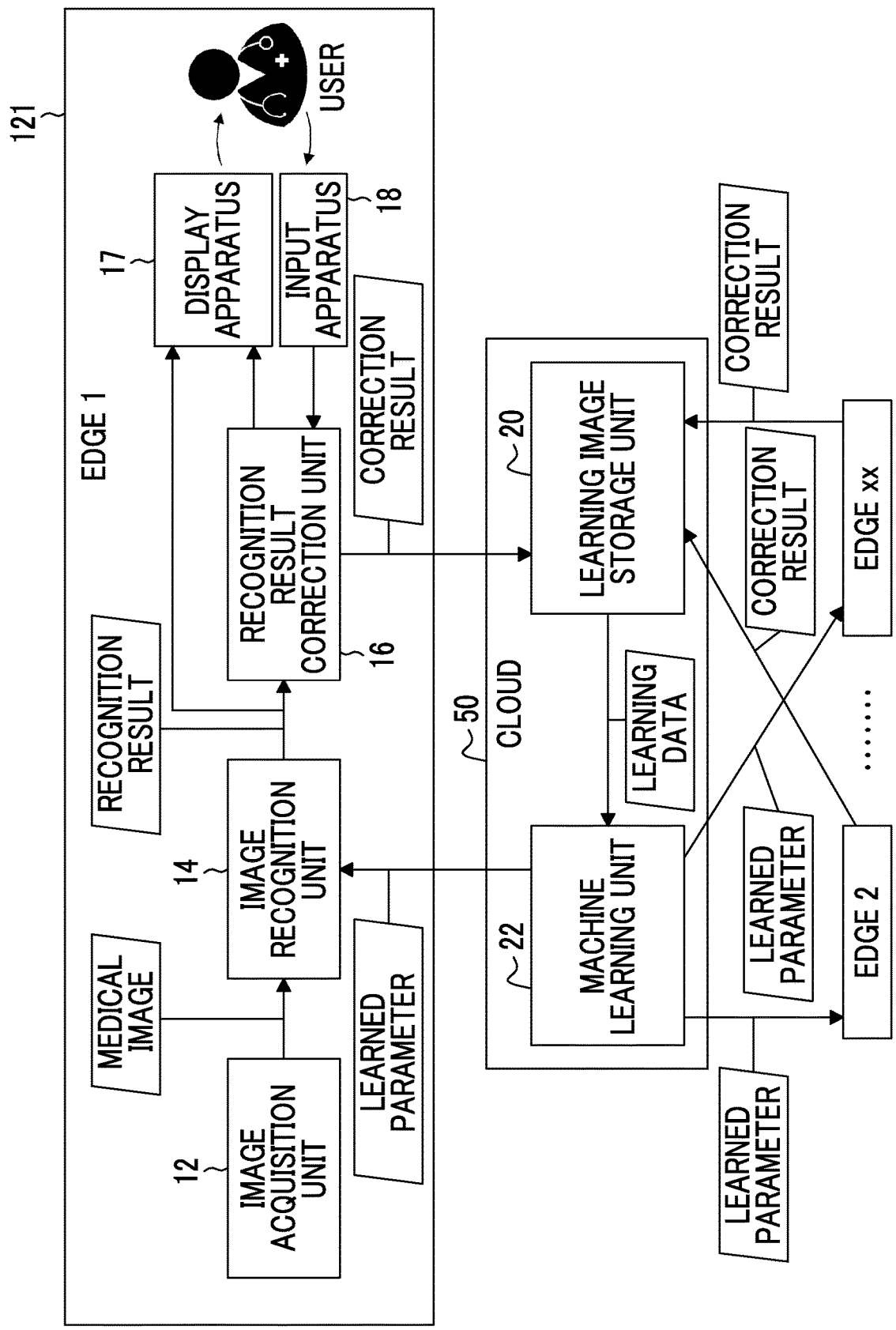
FIG. 11 is a block diagram illustrating a configuration of an image system according to an eighth embodiment.

FIG. 11 is a block diagram illustrating a configuration of an image system according to an eighth embodiment. The facility at which the image acquisition unit 12, the image recognition unit 14, and the recognition result correction unit 16 are installed is called the "edge", and the facility at which the learning image storage unit 20 and the machine learning unit 22 are installed is called the "cloud". A plurality of edges may be present. Each edge will be representatively described as an "edge 121".

Each edge 121 and the cloud 50 are connected through a network. In FIG. 11, illustration of the network is omitted. Data in which the recognition result is corrected by each user in each edge 121 is transmitted to the cloud 50 through the network and accumulated in the learning image storage unit 20 of the cloud 50.

In the cloud 50, learning is performed by the machine learning unit 22 based on the image accumulated in the learning image storage unit 20, and the parameter of the recognizer is updated. The cloud 50 distributes the updated parameter to the image recognition unit 14 of each edge 121.

In each edge 121, the parameter of the image recognition unit 14 is updated in accordance with the parameter distributed from the machine learning unit 22 of the cloud 50.

Each of the learning image storage unit 20 and the machine learning unit 22 may be installed at different remote facilities, or the learning image storage unit 20 and the machine learning unit 22 may be connected through the network.

According to the eighth embodiment, data of the rare case obtained from the plurality of edges 121 is accumulated in the learning image storage unit 20. Thus, multiple data can be collected, and the recognition performance can be further improved.

Each edge 121 illustrated in FIG. 11 is one example of a recognition apparatus having a function of generating learning data to be used in learning of a rare case. The learning image storage unit 20 illustrated in FIG. 11 is one example of a "learning data storage apparatus" storing the learning data generated by the recognition apparatus. In addition, the machine learning unit 22 illustrated in FIG. 11 is one example of a "machine learning apparatus" that performs learning using the learning data generated by the recognition apparatus.

<Example of Recognizer>

Figure 12:
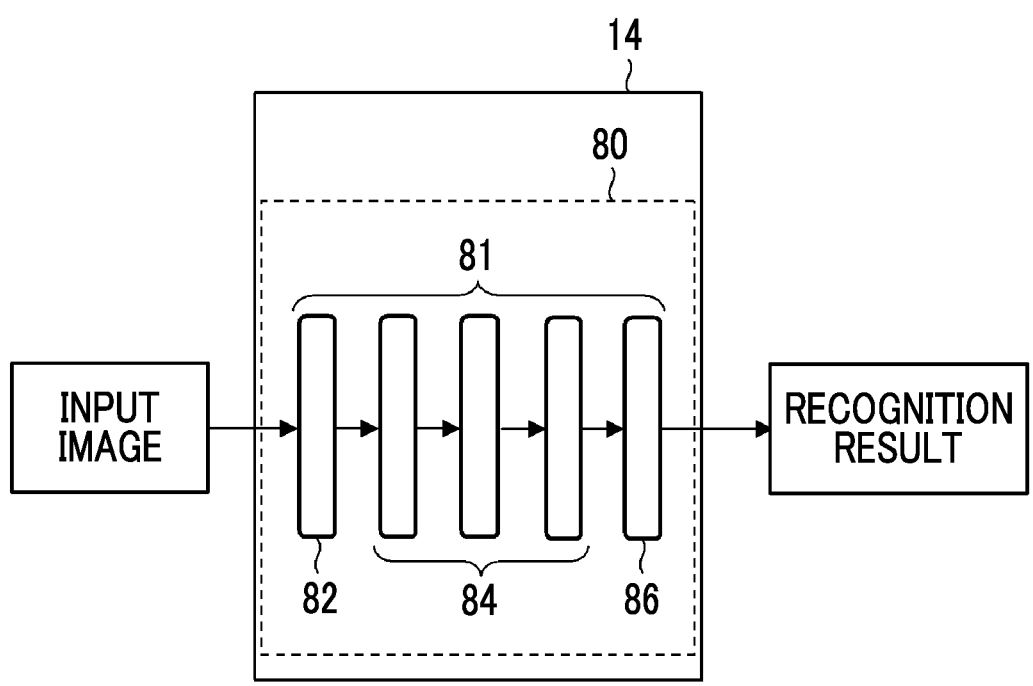
FIG. 12 is a conceptual diagram illustrating a configuration example of a recognizer.

FIG. 12 is a conceptual diagram illustrating a configuration example of the recognizer used in the image recognition unit 14. Here, a recognizer using a convolutional neural network that is a hierarchical neural network is illustrated. The neural network is a mathematical model of information processing that simulates the mechanism of the nervous system. Processing using the neural network can be implemented using a computer.

A neural network 81 constituting a recognizer 80 is a hierarchical neural network including an input layer 82, a plurality of intermediate layers 84, and an output layer 86. Each layer includes a plurality of "nodes". In FIG. 12, illustration of the nodes is omitted. A node belonging to a certain layer is connected to a node belonging to a layer on an output side from the certain layer. A connection weight is assigned to each inter-node connection between the nodes. Each connection weight is decided using machine learning.

The recognizer 80 comprises the learned neural network 81 in which the recognition performance is acquired using at least the first learning data set. The "learned neural network" is called the "learned model".

In the direction of flow of data from input toward output of the neural network 81, an input side is expressed as "front", and the output side is referred to as "rear".

The neural network 81 of the present example is a convolutional neural network including a combination of a convolutional layer and a pooling layer in a part of the plurality of intermediate layers 84. While the layer structure of the neural network 81 is illustrated in a simplified manner in FIG. 12, the number of layers of the intermediate layers 84 constituting the neural network 81, the processing content of each layer, and the arrangement order of each layer are not particularly limited, and a layer structure including various combinations may be employed.

The convolutional layer acquires a feature map by performing convolution calculation of applying a filter to a node present in a local region in the front layer. The convolutional layer performs feature extraction of extracting a featured intensity structure represented by the filter from the image.

The pooling layer performs pooling processing of aggregating local regions of the feature map output from the convolutional layer into a representative value. The pooling layer generates a new feature map of which the resolution is decreased by reducing the feature map output from the convolutional layer. The pooling layer provides robustness (decreases sensitivity to a positional change) such that a target feature amount extracted by the convolutional layer is not affected by a positional change.

The neural network 81 may include one or more of at least one type of layer of a normalization layer or a fully connected layer besides the convolutional layer and the pooling layer. In addition, each layer of the intermediate layers 84 may include an activation function as necessary.

The normalization layer performs processing of normalizing the intensity of the image. For example, the normalization layer performs processing of local contrast normalization on at least one output of the output of the convolutional layer or the output of the pooling layer.

The fully connected layer is a layer in which all nodes between adjacent layers are connected. The fully connected layer may be arranged near the output layer. For example, the fully connected layer connects the feature map from which a feature is extracted through the convolutional layer and the pooling layer to one node, and outputs a feature variable using the activation function. Generally, in the convolutional neural network, one or more fully connected layers are arranged between the last pooling layer and the output layer.

The output layer 86 performs class classification using, for example, a softmax function based on the output from the fully connected layer.

In a case where the image is input into the image recognition unit 14, processing is performed by the learned neural network 81, and the recognition result is output.

<Configuration Example of Machine Learning Unit>

Figure 13:
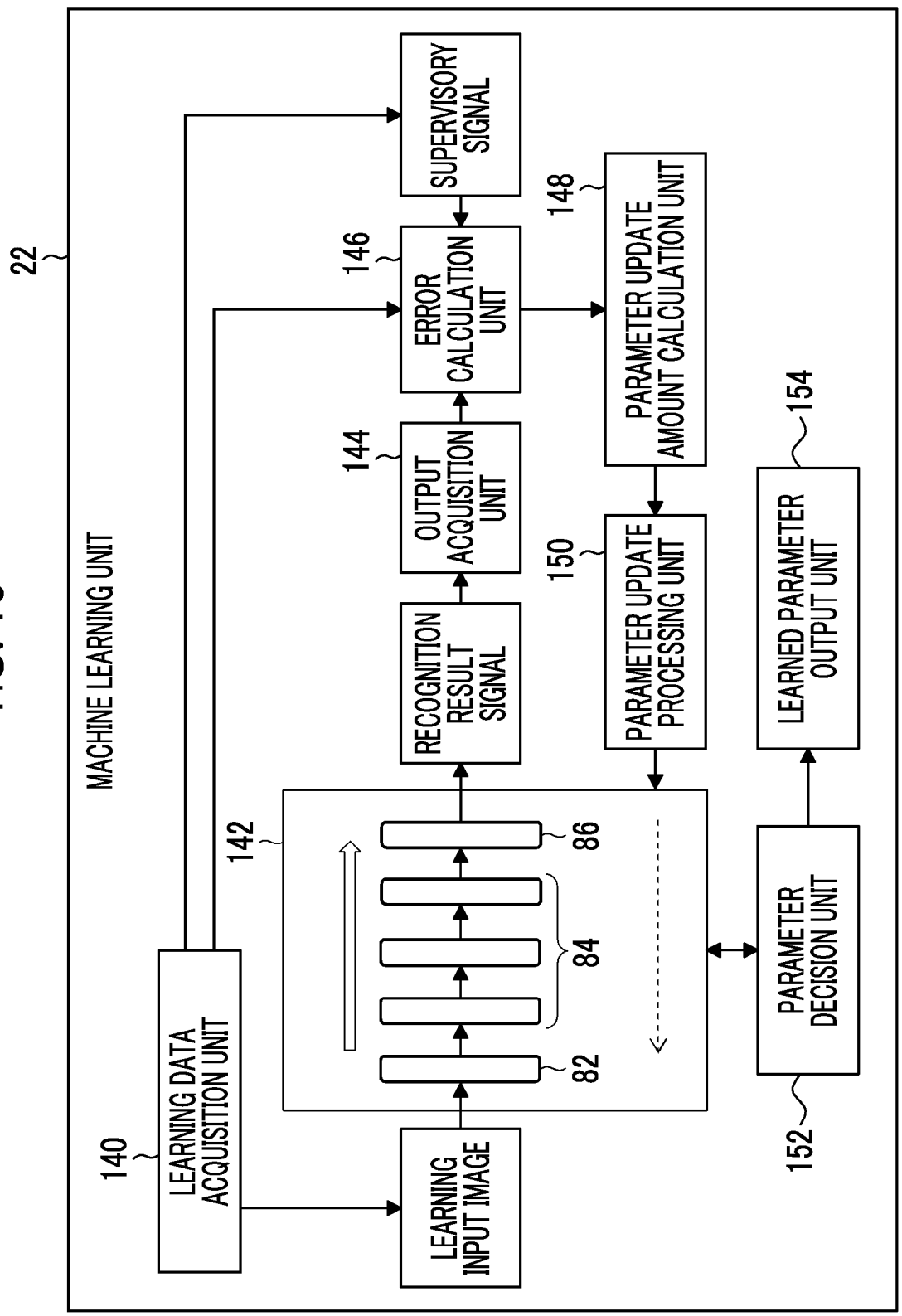
FIG. 13 is a block diagram illustrating functions of the machine learning unit.

FIG. 13 is a block diagram illustrating functions of the machine learning unit 22. The machine learning unit 22 includes a learning data acquisition unit 140, a learning recognizer 142, an output acquisition unit 144, an error calculation unit 146, a parameter update amount calculation unit 148, a parameter update processing unit 150, a parameter decision unit 152, and a learned parameter output unit 154. A display apparatus and an input apparatus, not illustrated, may be connected to the machine learning unit 22.

The learning data acquisition unit 140 is an interface for acquiring the learning data from the learning image storage unit 20. For example, the learning data acquisition unit 140 may be a communication interface for connection to the network. A learning input image of the learning data acquired through the learning data acquisition unit 140 is input into the learning recognizer 142.

The learning recognizer 142 is a recognizer comprising the same configuration as the recognizer 80 of the image recognition unit 14. The learning recognizer 142 performs the recognition processing using the learning input image as an input signal and outputs the recognition result signal.

The output acquisition unit 144 acquires the recognition result signal output from the neural network of the learning recognizer 142. The recognition result signal is input into the error calculation unit 146 through the output acquisition unit 144. The output acquisition unit 144 may be an input unit of the error calculation unit 146.

The error calculation unit 146 calculates an error between a resonance signal corresponding to the learning input image input in the learning recognizer 142 and the recognition result signal actually obtained from the learning recognizer 142. In the case of a form of using the error weight coefficient, the error calculation unit 146 calculates the weighted error using the error weight coefficient set for the learning input image. The error calculated by the error calculation unit 146 is transmitted to the parameter update amount calculation unit 148.

The parameter update amount calculation unit 148 calculates an update amount of a parameter of the neural network of the learning recognizer 142 based on the error (weighted error) calculated by the error calculation unit 146. For example, the parameter update amount calculation unit 148 calculates the update amount of the parameter in units of minibatches. The "parameter" includes a filter coefficient (connection weight) of the filter used in the processing of each layer, a bias of the node, and the like in the neural network.

The parameter update processing unit 150 performs processing of updating the parameter of the neural network of the learning recognizer 142 in accordance with the update amount calculated by the parameter update amount calculation unit 148.

A white arrow illustrated in the block of the learning recognizer 142 in FIG. 13 indicates the direction of flow of data in the case of the recognition processing, and a broken line arrow indicates the direction of flow of feedback including the processing of updating the parameter based on learning.

The parameter decision unit 152 finishes learning in accordance with the predetermined learning finish condition and decides the parameter of the learning recognizer. The decided learned parameter is transmitted to the image recognition unit 14 through the learned parameter output unit 154.

The learned parameter output unit 154 is an output interface for outputting the learned parameter decided by the parameter decision unit 152 to the outside. For example, the learned parameter output unit 154 may be a communication interface or a signal output terminal.

<Example of Display Screen for Displaying Recognition Result and Receiving Correction>

Figure 14:
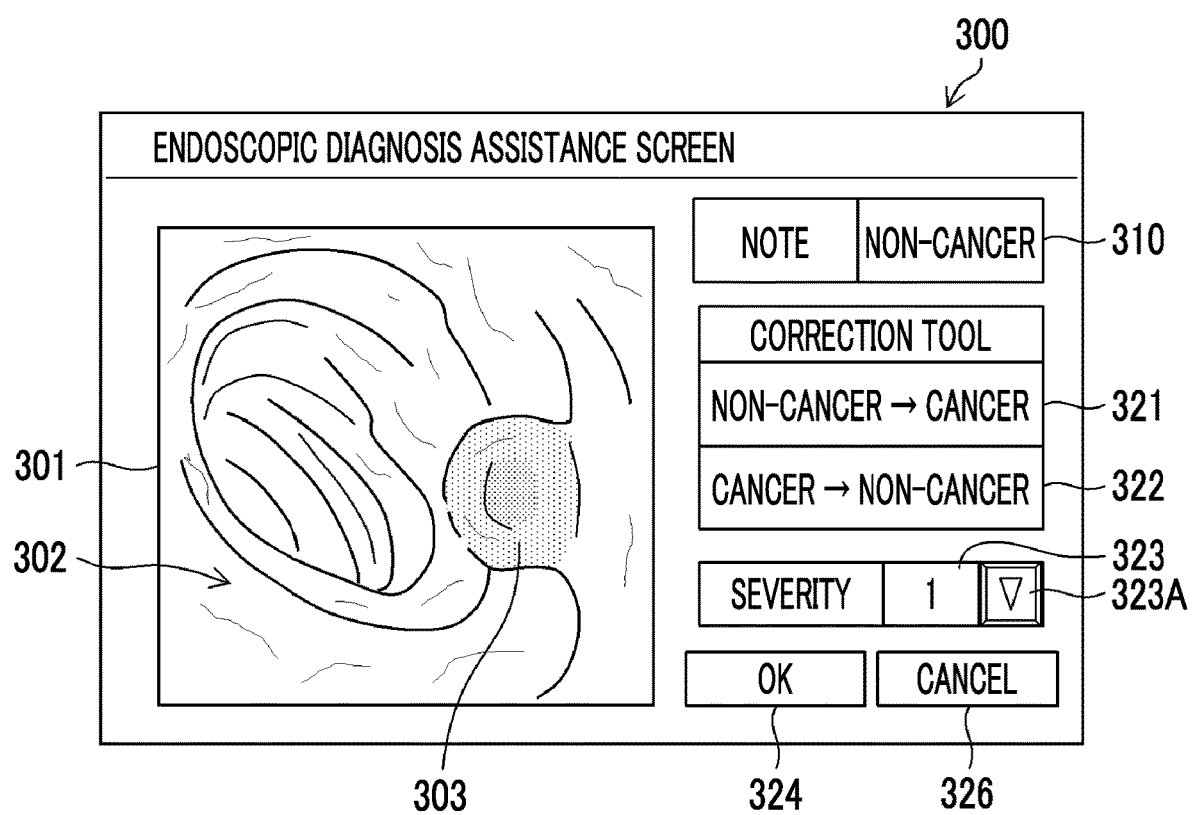
FIG. 14 is a diagram illustrating one example of an endoscopic diagnosis assistance screen displayed on a display apparatus.

FIG. 14 is a diagram illustrating one example of an endoscopic diagnosis assistance screen displayed on the display apparatus 17. A window 300 illustrated in FIG. 14 includes an image display area 301 and a recognition result display area 310. In the image display area 301, for example, an endoscope image 302 captured using an electronic endoscope is displayed in real time. In FIG. 14, an example in which a lesion region 303 is included in the image of the endoscope image 302 is illustrated. A plurality of lesion regions may be included in one image. In the recognition result display area 310, for example, information indicating "cancer" or "non-cancer" as the recognition result is displayed.

In addition, the window 300 includes correction instruction input buttons 321 and 322 as a correction tool, a severity input box 323, an OK button 324, and a cancel button 326. The "button" is a graphical user interface (GUI) button. The expression "push" for the GUI button includes an operation of inputting a command corresponding to the button like clicking or touching.

The correction instruction input button 321 is a button for inputting an instruction to correct the non-cancer recognition result to "cancer". In a case where the correction instruction input button 321 is pushed, the display content of the recognition result display area 310 is changed from "non-cancer" to "cancer". The correction instruction input button 321 is also used as a button for designating the category "false negative".

The correction instruction input button 322 is a button for inputting an instruction to correct the cancer recognition result to "non-cancer". In a case where the correction instruction input button 322 is pushed, the display content of the recognition result display area 310 is changed from "cancer" to "non-cancer". The correction instruction input button 322 is also used as a button for designating a category "false positive".

The severity input box 323 is a box for inputting the severity. In a case where a drop-down arrow 323A of the severity input box 323 is pushed, a drop-down menu, not illustrated, is displayed. A candidate that can be input in the severity input box 323 is presented in the drop-down menu. The user can input the severity by selecting a desired candidate from the drop-down menu.

The OK button 324 is a button for inputting a command to approve information contents displayed in the recognition result display area 310 and the severity input box 323.

In a case where the user pushes the OK button 324 after performing an operation of correcting the recognition result, processing of the correction instruction is executed, and the learning data for the additional learning is generated.

The cancel button 326 is a button that is selected in the case of canceling the correction instruction for the recognition result and the input of the severity. The user can provide the correction instruction and the input of the severity again by pushing the cancel button 326.

Instead of or in combination with the severity input box 323 illustrated in FIG. 14, a rarity input box for inputting the rarity of the clinical case may be disposed.

<Example of Aggregate of Learning Data Stored in Learning Image Storage Unit>

FIG. 15 is a conceptual diagram illustrating an example of the aggregate of learning data stored in the learning image storage unit 20. The learning image storage unit 20 stores the first learning data set used in the first learning and the learning data set of the rare case generated by correcting the recognition result. In the learning image storage unit 20, it is preferable to configure that the first learning data set and the learning data set of the rare case are grouped and managed. The learning data set of the rare case may be called a "second learning data set".

In each learning data, a data identification (ID) as a data identification code is assigned, and the input image, the correct answer, whether or not correction is made, and the weight are associated. While illustration is not provided in FIG. 15, the "severity" and/or the "rarity" may be further associated for the learning data of the rare case.

The "weight" is decided by reflecting "whether or not correction is made". Thus, the "weight" is understood as indicating whether or not correction is made. It is also possible to omit "whether or not correction is made" from the data structure illustrated in FIG. 15. Conversely, since the "weight" can be set from "whether or not correction is made" in accordance with a specific rule, "whether or not correction is made" can be left, and the "weight" can be omitted from the data structure illustrated in FIG. 15.

In the first learning data set, all learning data is "correction not made", and the "weight" is the common standard value "1.0". Thus, whether or not correction is made and the weight can be omitted for the first learning data set.

In the case of performing learning, it is preferable to use all learning data stored in the learning image storage unit 20. That is, it is preferable to use all learning data of the first learning data set and the learning data set of the rare case at least once in the unit of one epoch. The learning data belonging to the first learning data set and the learning data belonging to the learning data set of the rare case may coexist in the minibatch.

<Hardware Configuration of Each Processing Unit and Control Unit>

A hardware structure of processing units executing various types of processing such as the image acquisition unit 12, the image recognition unit 14, the recognition result correction unit 16, the machine learning unit 22, the contribution degree setting unit 32, the severity setting unit 36, and the rarity setting unit 40 described in each embodiment of the first embodiment to the eighth embodiment include various processors as illustrated below.

The various processors include a central processing unit (CPU) that is a general-purpose processor functioning as various processing units by executing a program, a graphics processing unit (GPU) that is a processor specialized in image processing, a programmable logic device (PLD) such as a field programmable gate array (FPGA) that is a processor having a circuit configuration changeable after manufacturing, a dedicated electric circuit such as an application specific integrated circuit (ASIC) that is a processor having a circuit configuration dedicatedly designed to execute a specific type of processing, and the like.

One processing unit may be configured with one of the various processors or may be configured with two or more processors of the same type or different types. For example, one processing unit may be configured with a plurality of FPGAs, a combination of a CPU and an FPGA, or a combination of a CPU and a GPU. In addition, a plurality of processing units may be configured with one processor. As an example of configuring the plurality of processing units with one processor, first, as represented by a computer such as a client or a server, a form of configuring one processor with a combination of one or more CPUs and software and causing the processor to function as the plurality of processing units is present. Second, as represented by a system on chip (SoC) or the like, a form of using a processor that implements the function of the entire system including the plurality of processing units using one integrated circuit (IC) chip is present. Accordingly, various processing units are configured using one or more of the various processors as a hardware structure.

Furthermore, the hardware structure of the various processors is more specifically an electric circuit (circuitry) into which circuit elements such as semiconductor elements are combined.

<Example of Hardware Configuration of Computer>

Figure 16:
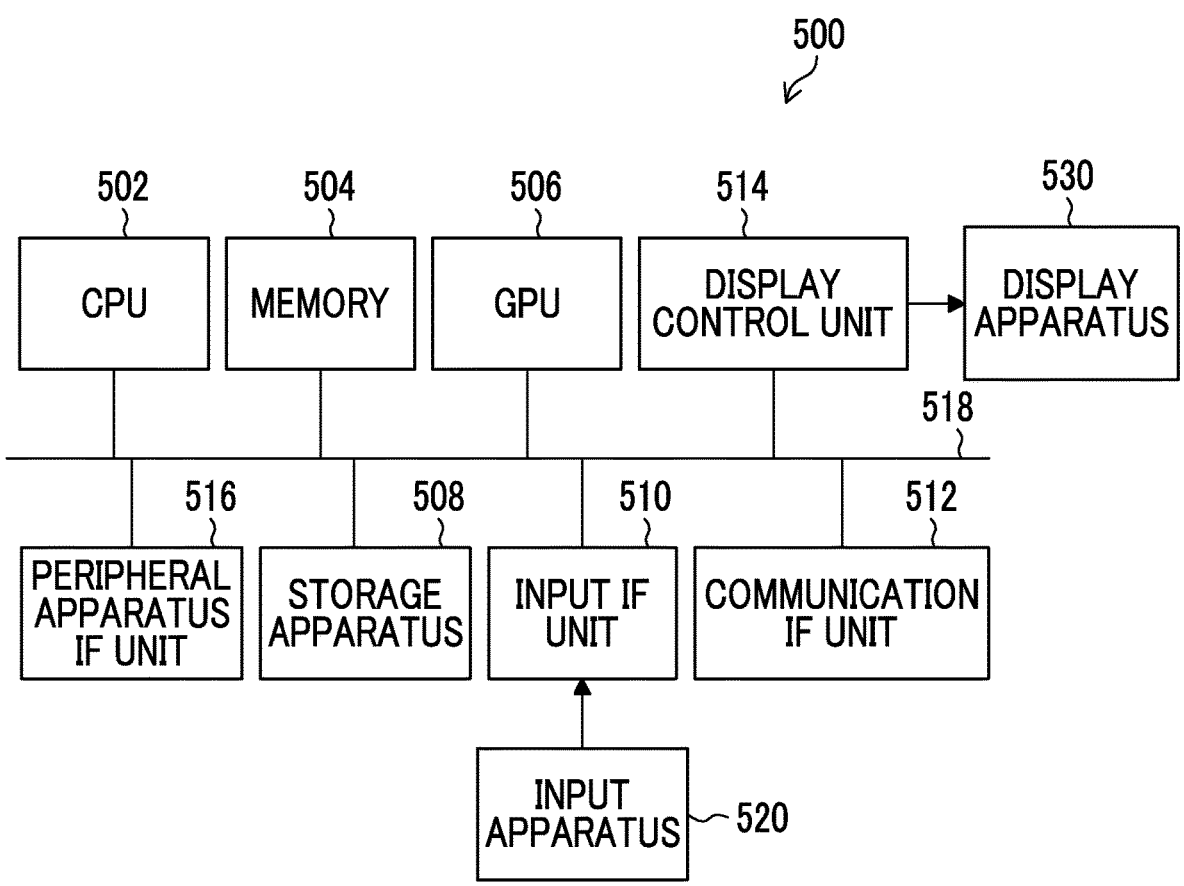
FIG. 16 is a block diagram illustrating a hardware configuration example of a computer.

FIG. 16 is a block diagram illustrating an example of a hardware configuration of a computer that can be used as an apparatus implementing a part or all of the functions of the image system according to the embodiment of the present invention. The computer includes computers of various forms such as a desktop type, a laptop type, or a tablet type. In addition, the computer may be a server computer or a microcomputer.

A computer 500 comprises a CPU 502, a memory 504, a GPU 506, a storage apparatus 508, an input interface unit 510, a communication interface unit 512 for network connection, a display control unit 514, a peripheral apparatus interface unit 516, and a bus 518. In FIG. 16, "IF" denotes an "interface".

The storage apparatus 508 may be configured using, for example, a hard disk apparatus. The storage apparatus 508 stores various programs, data, and the like necessary for image processing such as the learning processing and/or the recognition processing. By loading a program stored in the storage apparatus 508 into the memory 504 and causing the CPU 502 to execute the program, the computer functions as a section performing various types of processing prescribed by the program. The storage apparatus 508 can be used as the learning image storage unit 20.

An input apparatus 520 is connected to the input interface unit 510. A display apparatus 530 is connected to the display control unit 514. The input apparatus 520 and the display apparatus 530 may function as the input apparatus 18 and the display apparatus 17 described using FIG. 1.

<Program Operating Computer>

A program that causes the computer to implement at least one processing function of the function of generating the learning data, the recognition function using the recognition model, or the learning function described in the embodiments can be recorded on a computer readable medium that is a tangible non-transitory information storage medium such as an optical disk, a magnetic disk, or a semiconductor memory, and the program can be provided through the information storage medium. Alternatively, instead of the form of providing the program by storing the program in the tangible non-transitory information storage medium, a program signal can be provided as a download service using an electric communication line such as the Internet.

In addition, a part or all of at least one processing function of the function of generating the learning data, the recognition function, or the learning function described in the embodiments can be provided as an application server, and a service providing the processing function through the electric communication line can be performed.

Advantages of Embodiment of Present Invention

According to the embodiment of the present invention, the following effects are obtained.

(1) At actual medical sites, it is possible to efficiently collect the data of the rare case in which the recognition result is corrected by the user as the learning data for the additional learning while utilizing the recognition function of the image recognition unit 14.

(2) The recognition accuracy for the rare case can be preferentially improved by performing learning by relatively increasing the degree of contribution to learning from the learning data of the rare case generated by correcting the recognition result.

(3) The aggregate of learning data including data of the rare case obtained by the present embodiment may be used as a useful data set that helps improve the recognition performance for the rare case.

(4) In a case where data of an unknown rare case is acquired, the recognition performance of the recognizer can be updated as necessary, and diagnosis assistance useful for a doctor or the like can be performed.

Modification Example 1

The image acquired through the image acquisition unit 12 is not limited to the medical image obtained in real time from the electronic endoscope or the like and may be data of a still picture or a motion picture stored in an image storage server or the like, not illustrated.

Modification Example 2

While the image system handling the medical image has been illustrated in the embodiments, the present invention is not limited to the medical image and can be applied to an image system handling images of various applications or image types. In addition, the present invention is not limited to image recognition and can also be applied to a system performing processing such as voice recognition or language recognition.

Modification Example 3

A part or all of the functions of the image system 10 described using FIG. 1 may be provided in a workstation performing assistance of medical examination, treatment, diagnosis, or the like or may be provided in a work assistance apparatus assisting medical work. The work assistance apparatus may have a function of performing accumulation of clinical information, assistance of creating a diagnosis document, assistance of creating a report, and the like.

Combination of Embodiment, Modification Example, and Like

The constituents described in each embodiment and the constituents described in the modification examples can be appropriately used in combination, and a part of the constituents can be replaced.

[Others]

The constituents of the embodiments of the present invention described above can be appropriately changed, added, or removed without departing from the gist of the present invention. The present invention is not limited to the embodiments described above, and various modifications can be made by those having ordinary knowledge in the equivalent or relevant field within the technical idea of the present invention.

EXPLANATION OF REFERENCES

10: image system
12: image acquisition unit
14: image recognition unit
16: recognition result correction unit
17: display apparatus
18: input apparatus
20: learning image storage unit
22: machine learning unit
32: contribution degree setting unit
34: weight table storage unit
36: severity setting unit
38: conversion table storage unit
40: rarity setting unit
42: conversion table storage unit
50: cloud
80: recognizer
81: neural network
82: input layer
84: intermediate layer
86: output layer
102, 103, 104: image system
111, 121: edge
140: learning data acquisition unit
142: learning recognizer
144: output acquisition unit
146: error calculation unit
148: parameter update amount calculation unit
150: parameter update processing unit
152: parameter decision unit
154: parameter output unit
300: window
301: image display area
302: endoscope image
303: lesion region
310: recognition result display area
321, 322: correction instruction input button
323: severity input box
323A: drop-down arrow
324: OK button
326: cancel button
500: computer
502: CPU
504: memory
506: GPU
508: storage apparatus
510: input interface unit
512: communication interface unit
514: display control unit
516: peripheral apparatus interface unit
518: bus
520: input apparatus
530: display apparatus
S12 to S24: step of recognition processing and processing of generating learning data
S32 to S44: step of learning processing

What is claimed is:

1. A data processing apparatus comprising:
a processor configured to:
acquire data to be processed;
receive an input of the data, and output a recognition result for the data, using a recognition model that learns using a learning data set;
correct the recognition result in accordance with an instruction from a user; and
perform learning of the recognition model using the data in which the recognition result is corrected,
wherein the processor performs learning of the recognition model by setting a degree of contribution to learning from the data in which the recognition result is corrected to be higher than a degree of contribution to learning of the recognition model from learning data included in the learning data set.

2. The data processing apparatus according to claim 1, wherein the data being acquired is an image, and the processor is used as an image processing apparatus performing a task of image recognition.

3. The data processing apparatus according to claim 2, wherein the image is a medical image.

4. The data processing apparatus according to claim 1, wherein the recognition model is configured using a convolutional neural network.

5. The data processing apparatus according to claim 1, further comprising:
a storage apparatus that stores learning data including the data in which the recognition result is corrected, and a supervisory signal corresponding to the data.

6. The data processing apparatus according to claim 5, wherein contribution degree information indicating the degree of contribution in a case of being used in learning is assigned to the learning data stored in the storage apparatus.

7. The data processing apparatus according to claim 5, wherein the learning data set used in learning of the recognition model is stored in the storage apparatus.

8. The data processing apparatus according to claim 1, wherein the processor evaluates an error between a recognition result signal indicating the recognition result and a supervisory signal and updates a parameter of the recognition model based on the error.

9. The data processing apparatus according to claim 8, wherein the degree of contribution is represented by an error weight coefficient by which the error is multiplied.

10. The data processing apparatus according to claim 1, wherein the degree of contribution is represented by the number of times of use of the learning data in learning.

11. The data processing apparatus according to claim 1, wherein the processor sets the degree of contribution in a case of being used in learning for the data in which the recognition result is corrected.

12. The data processing apparatus according to claim 11, wherein the processor sets the degree of contribution depending on a category of a correction result based on the instruction from the user.

13. The data processing apparatus according to claim 11, wherein the processor variably sets the degree of contribution depending on an input from the user.

14. The data processing apparatus according to claim 13, wherein the processor receives an input of information indicating at least one of severity or rarity of the data in which the recognition result is corrected, and
the processor stepwise sets the degree of contribution depending on at least one of the severity or the rarity input through the correction.

15. A recognition apparatus comprising:
a processor configured to:
acquire data to be processed;
receive an input of the data, and output a recognition result for the data, using a recognition model that learns using a learning data set; and
correct the recognition result in accordance with an instruction from a user,
wherein the processor generates learning data for additional learning including the data in which the recognition result is corrected and a supervisory signal corresponding to the data, and generates correction information indicating that the recognition result is corrected for the data in which the recognition result is corrected,
wherein the processor generates contribution degree information indicating a degree of contribution to learning of the recognition model in a case of using the data in which the recognition result is corrected in learning, and wherein the degree of contribution to learning from the data in which the recognition result is corrected is set to be higher than a degree of contribution to learning of the recognition model from learning data included in the learning data set.

16. The recognition apparatus according to claim 15, further comprising:
a storage apparatus that stores the learning data and the correction information.

17. A learning data storage apparatus storing the learning data and the correction information generated by the recognition apparatus according to claim 15.

18. The learning data storage apparatus according to claim 17,
wherein an aggregate of the learning data having a data structure including the data in which the recognition result is corrected,
the supervisory signal corresponding to the data in which the recognition result is corrected, and
the contribution degree information indicating the degree of contribution to learning of the recognition model in a case of using the data in which the recognition result is corrected in learning is stored.

19. The learning data storage apparatus according to claim 18,
wherein the data structure further includes information on at least one of severity of a lesion or rarity of a clinical case.

20. A machine learning apparatus that generates a parameter of the recognition model using the learning data generated by the recognition apparatus according to claim 15,
wherein the machine learning apparatus performs learning of the recognition model by setting the degree of contribution to learning from the data in which the recognition result is corrected to be higher than the degree of contribution to learning of the recognition model from learning data included in the learning data set.

21. A data processing method comprising:
a data acquisition step of acquiring data to be processed;
a recognition step of receiving an input of the data acquired in the data acquisition step and outputting a recognition result for the data, using a recognition model that learns using a learning data set;
a recognition result correction step of correcting the recognition result in the recognition step in accordance with an instruction from a user; and
a machine learning step of performing learning of the recognition model using the data in which the recognition result is corrected in the recognition result correction step,
wherein in the machine learning step, learning of the recognition model is performed by setting a degree of contribution to learning from the data in which the recognition result is corrected to be higher than a degree of contribution to learning of the recognition model from learning data included in the learning data set.

22. A non-transitory, computer-readable recording medium which records commands that, when read by a computer, cause the computer to execute:
a data acquisition step of acquiring data to be processed;
a recognition step of receiving an input of the data acquired in the data acquisition step and outputting a recognition result for the data, using a recognition model that learns using a learning data set;
a recognition result correction step of correcting the recognition result in the recognition step in accordance with an instruction from a user; and
a machine learning step of performing learning of the recognition model using the data in which the recognition result is corrected in the recognition result correction step,
wherein in the machine learning step, learning of the recognition model is performed by setting a degree of contribution to learning from the data in which the recognition result is corrected to be higher than a degree of contribution to learning of the recognition model from learning data included in the learning data set.

* * * * *